US012357591B2

(12) United States Patent
Rawas-Qalaji

(10) Patent No.: US 12,357,591 B2
(45) Date of Patent: Jul. 15, 2025

(54) SUBLINGUAL EPINEPHRINE COMPOSITIONS INCLUDING PH-MODIFYING EXCIPIENTS AND PENETRATION ENHANCERS AND METHODS FOR USE THEREOF

(71) Applicant: Nova Southeastern University, Fort Lauderdale, FL (US)

(72) Inventor: Mutasem Rawas-Qalaji, Fort Lauderdale, FL (US)

(73) Assignee: Nova Southeastern University, Fort Lauderdale, FL (US)

( * ) Notice: Subject to any disclaimer, the term of this patent is extended or adjusted under 35 U.S.C. 154(b) by 785 days.

(21) Appl. No.: 17/285,711

(22) PCT Filed: Oct. 18, 2019

(86) PCT No.: PCT/US2019/056967
§ 371 (c)(1),
(2) Date: Apr. 15, 2021

(87) PCT Pub. No.: WO2020/081952
PCT Pub. Date: Apr. 23, 2020

(65) Prior Publication Data
US 2022/0000806 A1 Jan. 6, 2022

Related U.S. Application Data

(60) Provisional application No. 62/748,117, filed on Oct. 19, 2018.

(51) Int. Cl.
*A61K 31/137* (2006.01)
*A61K 9/00* (2006.01)
*A61K 47/12* (2006.01)
*A61K 47/20* (2006.01)

(52) U.S. Cl.
CPC .......... *A61K 31/137* (2013.01); *A61K 9/0056* (2013.01); *A61K 9/006* (2013.01); *A61K 47/12* (2013.01); *A61K 47/20* (2013.01)

(58) Field of Classification Search
None
See application file for complete search history.

(56) References Cited

U.S. PATENT DOCUMENTS

| | | | |
|---|---|---|---|
| 5,143,731 A | 9/1992 | Viegas et al. | |
| 5,223,614 A | 6/1993 | Schromm et al. | |
| 5,567,439 A | 10/1996 | Myers et al. | |
| 5,587,172 A | 12/1996 | Cherukuri et al. | |
| 5,622,716 A | 4/1997 | Barth | |
| 5,622,717 A | 4/1997 | Fuisz | |
| 5,654,003 A | 8/1997 | Fuisz et al. | |
| 5,871,781 A | 2/1999 | Myers et al. | |
| 6,024,981 A | 2/2000 | Khankari et al. | |
| 6,221,392 B1 | 4/2001 | Khankari et al. | |
| 6,264,981 B1 | 7/2001 | Zhang et al. | |
| 6,309,663 B1 | 10/2001 | Patel et al. | |
| 6,368,625 B1 | 4/2002 | Siebert et al. | |
| 6,833,377 B2 | 12/2004 | Serdyuk | |
| 9,877,921 B2 | 1/2018 | Rawas-Qalaji et al. | |
| 10,159,656 B2 | 12/2018 | Rawas-Qalaji | |
| 10,568,836 B2 | 2/2020 | Rawas-Qalaji | |
| 11,246,843 B2 | 2/2022 | Rawas-Qalaji et al. | |
| 2003/0021841 A1 | 1/2003 | Matharu et al. | |
| 2003/0216413 A1 | 11/2003 | Root-Bernstein et al. | |
| 2004/0076588 A1 | 4/2004 | Batycky et al. | |
| 2004/0234611 A1 | 11/2004 | Ahlheim et al. | |
| 2005/0130935 A1 | 6/2005 | Weidner | |
| 2006/0093677 A1 | 5/2006 | Chickering | |
| 2007/0059361 A1 | 3/2007 | Rawas-Qalaji | |
| 2007/0092553 A1 | 4/2007 | Tengler | |
| 2007/0122465 A1 | 5/2007 | Desai et al. | |
| 2007/0154549 A1 | 7/2007 | Morton et al. | |
| 2007/0020216 A1 | 8/2007 | Rawas-Qalaji | |
| 2007/0202163 A1* | 8/2007 | Rawas-Qalaji | A61K 31/137 514/649 |
| 2007/0293580 A1 | 12/2007 | Hill | |
| 2008/0032934 A1 | 2/2008 | Behnke et al. | |
| 2008/0069779 A1 | 3/2008 | Tamarkin et al. | |
| 2008/0226717 A1* | 9/2008 | Oury | A61P 35/04 427/2.14 |

(Continued)

FOREIGN PATENT DOCUMENTS

| | | |
|---|---|---|
| CN | 101669917 | 3/2010 |
| CN | 104666401 A | 6/2015 |

(Continued)

OTHER PUBLICATIONS

International Preliminary Report and Written Opinion dated May 1, 2014 for PCT/US2013/045836.
International Search Report dated Dec. 22, 2006, Written Opinion dated Dec. 22, 2006 and International Prelim Report on Patentability dated Dec. 10, 2007, for PCT/CA06/001472.
International Search Report dated Apr. 29, 2008, Written Opinion dated Apr. 29, 2008 and International Prelim Report on Patentability dated Apr. 11, 2009, for PCT/CA08/00197.
Office action dated Mar. 16, 2009 for U.S. Appl. No. 11/672,503, 8 pages.
Written Opinion dated Jan. 11, 2013 and International Prelim Report on Patentability dated Apr. 22, 2014, for PCT/US2012/061074.
International Search Report dated Jan. 11, 2013 for PCT/US2012/061074.

(Continued)

Primary Examiner — H. Sarah Park
(74) Attorney, Agent, or Firm — Fleit Intellectual Property Law; Paul D. Bianco; Katharine Davis Wong

(57) ABSTRACT

The invention provides sublingual epinephrine compositions including epinephrine fine particles formulated with pH-modifying excipients and penetration enhancers. The sublingual compositions are used to control absorption of epinephrine at the site of delivery in an oral cavity. The invention also provides methods for therapeutic use of the sublingual compositions for treatment of conditions responsive to epinephrine and/or for increasing sublingual bioavailability of epinephrine.

5 Claims, 4 Drawing Sheets

(56) References Cited

U.S. PATENT DOCUMENTS

| | | |
|---|---|---|
| 2009/0263476 A1 | 10/2009 | Jobodevairkkam |
| 2010/0035800 A1 | 2/2010 | Desai et al. |
| 2010/0291160 A1 | 11/2010 | Carver et al. |
| 2011/0097284 A1 | 4/2011 | Bottner et al. |
| 2011/0182005 A1 | 7/2011 | Yuan |
| 2011/0182805 A1 | 7/2011 | Desimone |
| 2011/0223203 A1 | 9/2011 | Berkland et al. |
| 2011/0250278 A1 | 10/2011 | Yuan |
| 2012/0322884 A1 | 12/2012 | Rawas-Qalaji |
| 2014/0242177 A1 | 8/2014 | Rawas-Qaiaji |
| 2014/0364513 A1 | 12/2014 | Park et al. |
| 2015/0164827 A1 | 6/2015 | Rawas-Qalaji et al. |
| 2016/0045457 A1 | 2/2016 | Rawas-Qalaji |
| 2016/0374966 A1* | 12/2016 | Rawas-Qalaji .......... A61K 9/14 514/653 |
| 2017/0000735 A1 | 1/2017 | Rawas et al. |
| 2017/0020827 A1* | 1/2017 | Rawas-Qalaji ........ A61K 9/006 |
| 2017/0071881 A1 | 3/2017 | Rawas-Qalaji et al. |
| 2017/0079907 A1 | 3/2017 | Potta et al. |
| 2018/0110763 A1 | 4/2018 | Dutt et al. |
| 2018/0147145 A1 | 5/2018 | Rawas-Qalaji et al. |
| 2019/0125698 A1 | 5/2019 | Rawas-Qalaji |
| 2019/0231716 A1 | 8/2019 | Rawas-Qalaji |
| 2022/0008060 A1 | 1/2022 | Rawas-Qalaji |

FOREIGN PATENT DOCUMENTS

| | | |
|---|---|---|
| CN | 104666401 A1 | 6/2015 |
| CN | 104666407 | 6/2015 |
| EP | 0159237 | 10/1985 |
| EP | 2753321 A1 | 7/2014 |
| EP | 2976072 | 5/2021 |
| JP | 2012-526840 A | 11/2012 |
| JP | 2012526840 | 11/2012 |
| WO | 1994/09762 | 11/1993 |
| WO | 2005/63203 | 12/2004 |
| WO | 2007/028247 | 3/2007 |
| WO | 2007/028247 A1 | 3/2007 |
| WO | 2007/143674 | 12/2007 |
| WO | 2007/143674 A2 | 12/2007 |
| WO | 2007/143674 A3 | 12/2007 |
| WO | 2008058755 A1 | 5/2008 |
| WO | 2008-095284 | 8/2008 |
| WO | 2008/095284 A1 | 8/2008 |
| WO | 2011/109340 | 9/2011 |
| WO | 2011109340 A1 | 9/2011 |
| WO | 2013-059629 | 4/2013 |
| WO | 2013/059629 A1 | 4/2013 |
| WO | 2014/007972 | 1/2014 |
| WO | 2014/153559 | 9/2014 |
| WO | 2014/153559 A1 | 9/2014 |
| WO | 2020/081952 A1 | 4/2020 |

OTHER PUBLICATIONS

International Prelim Report on Patentability dated Sept 4, 2012 for PCT/US2011/26604.
Office action dated Mar. 13, 2009 for U.S. Appl. No. 11/530,360.
For U.S. Appl. No. 13/582,346 office actions dated Sep. 12, 2013; Feb. 7, 2014 response dated Dec. 12, 2013.
European Patent Application No. 21170027.3 (Divisional of European Patent Application No. 14768584.6): Communication from European Patent Office dated Aug. 2, 2023 Response filed Jan. 23, 2024.
Office action for European Patent Application No. 13812628.9, dated Mar. 29, 2023.
Korenblat P, Lundie MJ, Dankner RE, Day JH. A retrospective study of epinephrine administration for anaphylaxis: how many doses are needed? Allergy Asthma Proc. 1999;20(6):383-6.
Sicherer SH, Forman JA, Noone SA. Use assessment of self-administered epinephrine among food-allergic children and pediatricians. Pediatrics. 2000;105(2):359-62.
Hoffman BB, Taylor P. Neurotransmission: The Autonomic and Somatic Motor Nervous Systems. In: Hardman JG, Limbird LE, Gilman AG, editors. Goodman & Gilman's The Pharmacological Basis of Therapeutics. 9 ed. New York: McGraw-Hill Companies, Inc.; 2001. p. 115-53.
Rawas-Qalaji MM, Simons FE, Simons KJ. Fast-disintegrating sublingual epinephrine tablets: effect of tablet dimensions on tablet characteristics. Drug Dev Ind Pharm. 2007;33(5):523-30.
Birudaraj R, Berner B, Shen S, Li X. Buccal permeation of buspirone: mechanistic studies on transport pathways. J Pharm Sci. 2005;94(1):70-8.
Goswami T, Li X, Jasti BR. Effect of Lipophilicity and Drug Ionization on Permeation Across Porcine Sublingual Mucosa. AAPS PharmSciTech. 2017;18(1):175-81.
Hassan N, Ahad A, Ali M, Ali J. Chemical permeation enhancers for transbuccal drug delivery. Expert Opin Drug Deliv. 2010;7(1):97-112.
Epinephrine: Chemical and Physical Properties Bethesda, MD, USA PubChem, National Center for Biotechnology Information, U.S. National Library of Medicine; 2018 [https://pubchem.ncbi.nlm.nih.gov/compound/5816#section=Chemical-and-Physical-Properties].
Attia MA, El-Gibaly I, Shaltout SE, Fetih GN. Transbuccal permeation, anti-inflammatory activity and clinical efficacy of piroxicam formulated in different gels. Int J Pharm. 2004;276(1-2):11-28.
Nicolazzo JA, Reed BL, Finnin BC. Assessment of the effects of sodium dodecyl sulfate on the buccal permeability of caffeine and estradiol. J Pharm Sci. 2004;93(2):431-40.
Duizer E, van der Wulp C, Versantvoort CH, Groten JP. Absorption enhancement, structural changes in tight unctions and cytotoxicity caused by palmitoyl carnitine in Caco-2 and IEC-18 cells. J Pharmacol Exp Ther. 1998;287(1):395-402.
Sutton SC, LeCluyse EL, Cammack L, Fix JA. Enhanced bioavailability of cefoxitin using palmitoyl L-carnitine. I. Enhancer activity in different intestinal regions. Pharm Res. 1992;9(2):191-4.
Swenson ES, Milisen WB, Curatolo W. Intestinal permeability enhancement: efficacy, acute local toxicity, and reversibility. Pharm Res. 1994;11(8):1132-42.
Office action for European Patent Application No. 13812628.9, dated Apr. 22, 2021.
RCE Response filed Aug. 5, 2021; for U.S. Appl. No. 16/225,609.
Notice of Allowance dated Sep. 7, 2021 with Interview Summary for U.S. Appl. No. 16/225,609.
Rawas-Qalaji, Sublingual epinephrine tablets versus intramuscular injection of epinephrine: Dose equivalence for potential theatment of anaphylaxis, vol. 117, #2, J Allergy Immunol Feb. 2006.
Rawas-Qalaji, Sublingual Diffusion of Epinephrine Microcrystals from Rapidly Disintegrating Tablets for the Potential First-Aid Treatment of Anaphylaxis: In Vitro and Ex Vivo Study, AAPS PharSciTech, vol. 16, No. 5, Oct. 2015 (10 pages).
Abdelbary, G. et al., "Determination of the in vitro disintegration profile of rapidly disintegrating tablets and correlation with oral disintegration," Int. J. Pharm. 292:29-41 (2005).
Allen, L., "Rapid-Dissolve Technology: An Interview with Lloyd V. Allen, Jr. PhD, RPh," Int. J. of Pharma. Compounding 7:449-450 (2003).
Aly, A. et al., "Superdistintegrants for Solid Dispersion to Produce Rapidly Disintegrating TenoxicamTablets via Comphor Sublimation," Pharma. Tech.7:68-78 (2005).
Aurora, J. and Pathak, V., "Oral Disintegrating Dosage Forms: An Overview," Drug Deliv. Technol. 5:50-54 (2005).
Bi, Y.X. et al., Evaluation of Rapidly Disintegrating Tablets Prepared by a Direct Compression Method, Drug Dev. Ind. Pharm. 25:571-581 (1999).
Bi, Y. et al., "Preparation and Evaluation of a Compressed Tablet Rapidly Disintegrating in the Oral Cavity," Chom, Pharm. Bull, 44:2121-2127 (1996).
Birudaraj, R. et al., "Buccal Permeation of Buspirone: Mechanistic Studies on Transport Pathways," J. Pharm. Sci. 94:70-78 (2004).
Chang, R. et al., "Fast-Dissolving Tablets," Pharm. Tech. 24:52-58 (2000).
Cunningham, F. et al., "Comparative Pharmacokinetics of Oral versus Sublingual Clonidine," J. Clin. Anesth, 6:430-433 (1994).

(56) References Cited

OTHER PUBLICATIONS

De Vries, M. et al., "Devements in Buccal Drug Delivery," Crit. Rev. Ther. Drug Carr. Syst. 8:271-303 (1991).
Dobetti, L., "Fast-Melting Tablets: Developments and Technologies," Pharmaceutical Technology Europe 12:32-42 (2000).
Dor, P. and Fix, J., "In Vitro Determination of DisintegrationTime of Quick-Dissolve Tablets Using a New Method," Pharm. Dev. Technol. 5:575-577 (2000).
El-Arini. S. and Clas, S., "Evaluation of Disintegration Testing of Different Fast Dissolving Tablets Using the Texture Analyzer," Pharm. Dev. Technol. 7:361-371 (2002).
Fell, J.T. and Newton, J.M., "Determination of Tablet Strength by the Diametral-Compression Test," J. Pharm. Sci. 59:688-691 (1970).
Ganhao, M. et al., "Evaluation of a simple plasma catecholamine extraction procedure prior to high-performance liquid chromatography and electrochemical detection," J. Chromatogr, 564:55-66 (1991).
Gu, X. et al., "Is Epinephrine Administration by Sublingual Tablet Feasible for the First-Aid Treatment of Anaphylaxis? A Proof-Of-Concept Study," Biopharm. Drug Dispos. 23:213-216 (2002).
Gu, X., et al., "Epinephrine Absorption after Different Routes of Administration in an Animal Model," Biopharm Drug Dispos. 20:401-405 (1999).
Hamilton, E. et al., "Advanced Orally Disintegrating Tablets Bring Signig=ficant Benefits to Patients & Products Life Cycles," Drug Deliv. Techno. 5:34-37 (2005).
Hedenus, P/ et al., "Characterisation of instantaneous water absorption properties of pharmaceutical excipients," Int. J. Pharm. 141:141-149 (2000).
Hjemdahl, P., "Catecholamine Measurements in Plasma by High-Performance Liquid Chromatography with Electrochemical Detection," Methods in Enzymol. 142:521-534 (1987).
Hjemdahl, P., "Inter-laboratory comparsion of plasma catecholamine determinations using several different assays," Acia Physiol. Scand, Suppl. 527:43-54 (1984).
Human Physiology: From Cells to Systems, Sherwood I., (ed.) Brooks/Cole/Thomson Learning: Belmont, CA, 2004; Chapter 16, pp. 591-645.
Ishikawa, T. et al., "Pharmacokinetics of Acetominophen from Rapidly Disintegrating Compressed Tablet Prepared Using Microcrystalline Cellulose (PH-M-06) and Spherical Sugar Granules," Chem Pharm. Bull, 49:230-232 (2001).
Ishikwawa, T. et al., "Preparation of Rapidly Disintegrating tablet Using New Types of Microcrystalline Cellulose (PH-M Series) and Low Substituted-Hydroxypropylcellulose or Spherical Sugar Granules by Direct Compression Mehod," Chem. Pharm. Bull. 49:134-139 (2001).
Kroboth, P/ et al., "Triazopam Pharmacokinetics After Intravenous, Oral, and Sublingual Administration," J. Clip, Psychopharmacol, 15:259-262 (1995).
Lieberman, P. et al., "Joint Task Force on Practice Parameters," J. Allergy Clin. Immunol, 115:S483-S523 (2005).
Lieberman, P., "Use of epinephrine in the treatment of anaphylaxis," Curr. Opin. Allergy Clin. Immunol. 3:313-318 (2003).
Mitra, A. et al., "Petides and Proteins—Buccal Absorption," Encyclopedia of Pharm. Tech., pp. 2081-2095 (2002).
Motwani, J. and Lipworth, B., "Clinical Pharmacokinetics of Drugs Administered Buccally and Sublingually," Clin. Pharmacokinet. 21:83-94 (1991).
Parakh, S.R. and Gothoskar, A.V., "A Review of Mouth Dissolving Tablet Technologies," Pharm. Tech. 27:92-100 (2003).
Price, T.M. et al., "Single-Dose Pharmacokinetics of Sublingual Versus Oral Administration of Micronized 17B-Estradiol," Obstet. Gynecol. 89: 340-345 (1997).
Rawas-Qalaji, M. et al., "Fast-Disintegrating Sublingual Epinephrine Tablets: Effects of Drug and Tablet Dimensions on Tablet Characteristics," AAPS 7(52):Abstract W5220 (2005).
Rawas-Qalaji, M. et al., "Sublingual epinephrine tablets versus intramuscular injection of epinephrine: Dose equivalence for potential treatment of anaphylaxis," J. Allergy Clin. Immunol, 177(2):398-403 (Feb. 2006).
Rawas-Qalaji, M. et al., "Fast-Disintegrating Sublingual Epinephrine Tablets: Effect of Epinephrine Load on Tablet Characteristics," AAPS PharmSciTech 7(2) Article 41: E1-E7 (2006).
Rawas-Qalaji, M. et al., "Fast-Disintegrating Sublingual Epinephrine Tablets: Long Term Stability Study," AAPS 7 (52) Abstract W5219 (2005).
Rawas-Qalaji, M. et al., "Formulation of Fast-Disintegrating Sublingual Epinephrine Tablets For The First-Aid Treatment Of Anaphylaxis Away From Health Care Facilities," AAPS 6(6) Abstract W4178 (2004).
Rawas-Qalaji, M. et al., "Evaluation Of The Effect Of Changing Tablet Dimensions On The Characteristics Of Fast-disintegrating Sublingual Epinephrine Tablets For The First-Aid Treatment Of Anaphylaxis Away From Health Care Facilities," AAPS 6(4) Abstract 4179 (2004).
Rawas-Qalaji, M. et al., "Epinephrine for the Treatment of Anaphylaxis: Do All 40mg Sublingual Epinephrine Tablet Formulations with Similar In Vitro Characteristics Have the Same Bioavailability?" Biopharm. Drug Dispos 27:427-435 (2006).
Sastry, S. et al., Drug Del. To the Oral Cavity: Molecule to Market, Chapter 13, pp. 311-316 (2005), eds. Taylor&Francis, CRC Press.
Sastry, S. et al., "Recent technological advances in oral drug delivery—a review," Pharm Sci. Technol. Today 3:138-145 (2000).
Scavone, J.M. et al., "The Pharmacokinetics and pharmacodynamics of sublingual and oral alprazolam in the post-prandial state," Eur. J. Clin. Pharmacol. 42:439-443 (1992).
Schiermeier, S. and Schmidt, P., "Fast dispersable ibuprofen tablets," Eur. J Phar. Sci. 15:295-305 (2002).
Sharma, N. et al., "Manufacturing Technology Choices for Mouth Dissolving Tablets," Pharma. Tech. North America 10-15 (2003).
Simons, F. Estelle, "First-aid treatment of anaphylaxis to food: Focus on epinephrine," J. Allergy Clin. Immunol. 113:837-844 (2004).
Simons, K.J. et al., "Sublingual epinephrine administration in humans: A preliminary study," J. Allergy Clin. Immunol. 113 (Suppl. 1):S260 (2004).
Simons, F. Estelle, "EpiPen Jr versus EpiPen in young children weighing 15 to 30 kg at risk for anaphylaxis," J. Allergy Clin. Ommunol. 109(1):171-175 (2002).
Simons, F. Estelle et al., "Outdated EpiPen and EpiPen Jr. autoinjectors: Past their Prime?" J. Allergy Clin. Immunol. 105:1025-1030 (2000).
Spendard, J. et al., "Placebo-Controlled Comparative Study of the Anxiolytic Activity and of the Pharmacokinetics of Oral and Sublingual Lorazepam in Generalized Anxiety," Biopharm. Drug Dispos. 9:457-464 (1988).
Sugimoto, M. et al., "The Preparation of Rapidly Disintegrating Tablets in the Mouth," Pharm. Dev. Technol. 6:487-493 (2001).
Verma, R. and Garg, S., "Current Status of Drug Delivery Technologies and Future Directions," Pharma. Technol. On-Line 25: 1-4 (2001).
International Search Report and Written Opinion dated Aug. 20, 2014 for PCT/US14/31579.
European Search Report dated Aug. 30, 2021; for European Patent Application No. 21170027.3.
Response filed Apr. 6, 2022 for European Patent Application No. 21170027.3.
For Canadian Patent Application No. 2,907,770, filed Mar. 24, 2014: Response for filed Jun. 9, 2021.
JP Office action for Japanese Patent Application No. 2021-521216, dated Oct. 3, 2023; with English translation.
Citric Acid Revised Handbook of Pharmaceutical Excipients Feb. 28, 2007.
S. Prajapati et al. Preparation and evaluation of sublingual tablets of zolmitriptan; International Journal of Pharmaceutical Investigation Jan. 2014; vol. 4.
Office Action dated Nov. 17, 2015 for EP 14-768584 (national stage of PCT/US2014/31579).

(56) References Cited

OTHER PUBLICATIONS

International Search Report dated Aug. 20, 2014, Written Opinion dated Aug. 20, 2014 and International Preliminary Examination Report dated Sep. 22, 2015 for PCT/US14/31579.
Ishikawa et al., 2001, Chem Pharm Bull 49: 230-23.
Price et al., 1997, Obstet Gynecol 89: 340-345.
Kroboth et al., 1995, J Clin Psychopharmacol 15: 259-262.
Cunningham et al., 1994, J Clin Anesth 6: 430-433.
Scavone et al., 1992, Eur J Clin Pharmacol 42: 439-443.
Spenard et al., 1988, Biopharm Drug Dispos 9: 457-464.
Mitra et al., 2002, Encyclopedia of Pharm. Tech., 2081-2095.
Joint Task Force on Practice Parameters, 2005, J Allergy Clin Immunol 115: S483-S523.
Lieberman, 2003, Curr Opin Allergy Clin Immunol 3: 313-318.
Simons, 2004, J Allergy Clin Immunol 113: 837-844, First-Aid Treatment of Anaphylaxis to Food, 8 pgs.
Simons, F.E.R. J Allergy Clin Immunol 124(4):625-636 2009, Anaphylaxis: Recent Advances in Assessment and Treatment, 12 pgs.
Simons, F.E.R. J Allergy Clin Immunol 125:S161-181 2010, Anaphylaxis, 21 pgs.
Simons, K.J. et al. Current Opinion in Clinical Immunology 10:354-361 2010, Epinephrine and Its use in Anaphylaxis, 8 pgs.
Connors et al., 1986, in Chemical Stability of Pharmaceuticals: A Handbook for Pharmacists, Wiley-Interscience Publication: New York.
Gu et al., 2002, Biopharm Drug Dispos 23: 213-216.
Simons et al., 2004, J Allergy Clin Immunol 113: 425-438, S260 Abstract.
Rawas-Qalaji et al. J Allergy Clin Immunol 117:398-403 2006.
Rawas-Qalaji et al. Biopharm Drug Disposition 27 (9):427-435 2006.
AAPS PharmSciTech 12:544-552,2011.
Rachid, O. et al. AAPS PharmSciTech 12(2):544-552 2011.
USP/NF. Physical Tests: Dissolution (711); 22/17 ed. Rockville, MD: United States Pharmaceutical Convention Inc; 2007.
Rachid, O. et al. AAPS PharmSciTech 11(2):550-557 2010.
Rawas-Qalaji, AAPS PharmSciTech. 2006;7(2): Article 41.
Motwani et al., 1991, Clin Pharmacokinet 21: 83-94.
Written Opinion mailed Apr. 29, 2011 for PCT/US11/26604 filed Mar. 1, 2010.
International Search Report mailed Apr. 29, 2011 for PCT/US11/26604 filed Mar. 1, 2010.
Written Opinion mailed Jan. 11, 2013 for PCT/US12/061074 filed Oct. 19, 2012.
International Search Report mailed Jan. 11, 2013 for PCT/US12/061074 filed Oct. 19, 2012.
International Search Report dated Jan. 16, 2014 for PCT/US2013/045836.
Written opinion dated Jan. 16, 2014 for PCT/US2013/045836.
Rawan-Qalaji et all, Development of Epinephrine Nanoparticles Using Chitosan for the Treatment of Anaphylaxis, Poster presentation at the 2011 AAPS Annual Meeting and Exposition, Oct. 23-27, 2011, Washington DC, Poster No. W4174.
Adrenaline into Melanin, Br Med J, May 29, 2971, 2(5760): 486.
Sigma-Aldrich, Material Safety Data Sheet, Version 3.2, printed May 1, 2012 (6 pages).
Saxena, Sublingual versus vaginal route of misoprostol for cervical ripening prior to surgical termination of first timrester abortions, Eur J Obstet Gynecol Reprod Biol Mar. 1, 2006, 125(1): 109-13, abstract.
For Canadian Patent Application No. 3116730: Examination Reprot dated Oct. 25, 2023 (4 pages) Response filed Feb. 26, 2024 (21 pages).
European Search Report for EP Application No. 19 87 2893; dated Jun. 28, 2022.
Office action for Canadian Patent Application No. 3, 169,368, dated Sep. 15, 2023.
Notice of Allowance dated Sep. 20, 2021 for U.S. Appl. No. 16/377,810.

Notice of Allowance dated Oct. 12, 2021 for Canadian Patent Application No. 2,853,084.
Decision to Grant dated Nov. 18, 2021; for European Patent Application No. 12842206.0.
Notice of Allowance dated Sep. 7, 2021 for U.S. Appl. No. 16/225,609.
Birudaraj et al., Buccal Permeation of Buspirone: Mechanistic Studies on Tramport Pathways, J Pharm Sci, vol. 94, Jan. 2005, p. 70-78.
European Patent Office Communication—Extended Search Report for European Patent Application No. 21170027.3, dated Aug. 30, 2021 (8 pages).
Mutasem M. Rawas-Qalaji et al., Fast Disintegrating Sublingual tablets; Effect of Epinephrine Load on Tablets Characteristics, AAPS PharmaSci Tech, 2006, p. E1-E7.
For Korean Patent Application No. 10-2021-7014434; Office action dated Oct. 16, 2024; English translation (14 pages).
https://pubchem.nchi.nim.nih.gov, Epinephrine Article PubChem 2025 (2 pages).
Office Action date Feb. 4, 2025 for U.S. Appl. No. 17/582,045 (16 pages).
Final Office Action for U.S. Appl. No. 15/882,399 dated Sep. 27, 2018.
Final Office Action dated Apr. 30, 2019, for U.S. Appl. No. 15/358,743 45 pages.
Response filed May 2, 2019, to Office Action from European Patent Office for EP Patent Application No. 14 768 584.6, 11 pages.
Examination Report for Canadian Patent Application No. 2,876,883, 4 pages; dated May 22, 2019.
European Search Report for EP Patent Application No. 12 842 206.0, dated Jul. 1, 2019.
Ting Qiao et al., Conjugation of Catecholamines on Magnetic nanoparticles coated with Sulfonated Chitosan; Science Direct, vol. 380, Issue 1-3, pp. 169-174; May 5, 2011.
For U.S. Appl. No. 16/377,810: Final Office Action dated Mar. 1, 2021.
Schianti et al, Rifampicin Nanoprecipiation using Flow Focusing Microfluidic Device, Journal of Nanomedicine & Nanotechnology, 2013, 6 pages.
For Canadian Patent Application No. 2,876,883, Response dated Nov. 22, 2019; Office Action dated Feb. 25, 2020; Response dated Aug. 25, 2020; Office Action dated Nov. 19, 2020; Response filed Mar. 18, 2021.
For Canadian Patent Application No. 2,907,770, filed Mar. 24, 2014: Office Action dated Feb. 9, 2021.
For U.S. Appl. No. 16/225,609: Response filed Aug. 19, 2020.
For EP Application 14 768 584.6 (regional stage of PCT/US2014/31579): response dated Sep. 19, 2018; office action dated Jan. 15, 2019; response dated May 2, 2109; office action dated Sep. 26, 2019; response dated Dec. 18, 2019; Office Action dated May 8, 2020; response filed Jul. 6, 2020.
For Canadian Patent Application No. 2,853,084: Response filed Mar. 12, 2020.
Office Action for U.S. Appl. No. 16/225,609 dated Oct. 8, 2019.
Merriam Webster Definition of "Microcrystal" dated Sep. 26, 2019.
Collins Dictionary Definition of "Microparticle" retrieved Sep. 26, 2019.
Office Action for U.S. Appl. No. 16/377,810, dated Oct. 9, 2019.
Office Action for Canadian Patent Application No. 2,853,084: dated Sep. 12, 2019.
Kemp SF, Lockey RF, Simons FE. Epinephrine: the drug of choice for anaphylaxis. A statement of the World Allergy Organization. Allergy 2008; 63:1061-70.
McLean-Tooke AP, Bethune CA, Fay AC, Spickett GP. Adrenaline in the treatment of anaphylaxis: what is the evidence? BMJ 2003; 327:1332-5.
Simons KJ, Simons FE. Epinephrine and its use in anaphylaxis: current issues. Curr Opin Allergy Clin Immunol 2010; 10:354-61.
Soar J, Pumphrey R, Cant A, Clarke S, Corbett A, Dawson P, et al. Emergency treatment of anaphylactic reactions—guidelines for healthcare providers. Resuscitation 2008; 77:157-69.

(56) References Cited

OTHER PUBLICATIONS

Simons FE. Epinephrine auto-injectors: first-aid treatment still out of reach for many at risk of anaphylaxis in the community. Ann Allergy Asthma Immunol 2009; 102:403-9.
Simons FER. Lack of worldwide availability of epinephrine autoinjectors for outpatients at risk of anaphylaxis. Ann Allergy Asthma Immunol 2005; 94:534-8.
Bredenberg S, Duberg M, Lennernas B, Lennernas H, Pettersson A, Westerberg M et al. In vitro and in vivo evaluation of a new sublingual tablet system for rapid oromucosal absorption using fentanyl citrate as active substance. Eur J Pharm Sci 2003; 20:327-34.
Glover ED, Glover PN, Franzon M, Sullivan CR, Cerullo CC, Howell RM, et al. A comparison of a nicotine sublingual Tablet and placebo for smoking cessation. Nicotine Tob Res 2002; 4:441-50.
Guez S. Efficacy of desensitization via the sublingual route in mite allergy. Chem Immunol Allergy 2003; 82:62-76.
Rawas-Qalaji MM, Simons FE, Simons KJ. Sublingual epinephrine tablets versus intramuscular injection of epinephrine: Dose equivalence for potential treatment of anaphylaxis. J Allergy Clin Immunol 2006; 117:398-403.
Rawas-Qalaji MM, Simons FE, Simons KJ. Epinephrine for the treatment of anaphylaxis: do all 40 mg sublingual epinephrine tablet formulations with similar in vitro characteristics have the same bioavailability? Biopharm Drug Dispos 2006; 27:427-35.
Saxena P, Salhan S, Sarda N. Sublingual versus vaginal route of misoprostol for cervical 20 ripening prior to surgical termination of first trimester abortions. Eur J Obstet Gynecol Reprod Biol, 125:109-113, 2006.
Chapter 8, Neurotransmission: The Autonomic and Somatic Motor Nervous Systems In Goodman & Gilman's The Pharmacological Basis of Therapeutics. 12 ed., 16 pages, 2011.
Rachid O, Simons FE, Rawas Qalaji M, Simons KJ. An electronic tongue: evaluation of the masking efficacy of sweetening and/or flavoring agents on the bitter taste of epinephrine. AAPS PharmSciTech 2010; 11:550-7.
Rawas Qalaji MM, Simons FE, Simons KJ. Fast-disintegrating sublingual epinephrine 30 tablets: effect of tablet dimensions on tablet characteristics. Drug Dev Ind Pharm 2007; 33:523-30.
Rawas-Qalaji MM, Simons FER, Simons KJ. Fast-Disintegrating Sublingual Tablets: Effect of Epinephrine Load on Tablet Characteristics. AAPS PharmSciTech 2006; 7: Article 41.
Muller RH, Gohla S, Keck CM. State of the art of nanocrystals â€" Special features, production, nanotoxicology aspects and intracellular delivery. European Journal of Pharmaceutics and Biopharmaceutics; 78:1-9.
USP/NF. Physical Tests: Uniformity of Dosage Units (905). 31/26 ed. Rockville, MD: United States Pharmacopeial Convention, Inc.; 2008.
USP/NF. Official Monograph: Epinephrine Injection. 31/26 ed. Rockville, MD: United States Pharmacopeial Convention, Inc.; 2008.
USP/NF. Physical Tests: Tablet Friability (1216). 31/26 ed. Rockville, MD: United States Pharmacopeial Convention, Inc.; 2008.
Olfert ED, Cross BM, McWilliam AA. Guide to the care and use of experimental animals. 2 ed. Ottawa: Canadian Council on Animal Care; 1993.
Hjemdahl P. Inter-laboratory comparison of plasma catecholamine determinations using several different assays. Acta Physiol Scand Suppl 1984; 527:43-54.
Hjemdahl P. Catecholamine measurements in plasma by high-performance liquid chromatography with electrochemical detection. Methods Enzymol 1987; 142:521-34.
Ganhao MF, Hattingh J, Hurwitz ML, Pitts NI. Evaluation of a simple plasma catecholamine extraction procedure prior to high-performance liquid chromatography and electrochemical detection. J Chromatogr 1991; 564:55-66.

Rachid O, Rawas-Qalaji M, Simons FE, Simons KJ. Rapidly-disintegrating sublingual tablets of epinephrine: role of non-medicinal ingredients in formulation development. Eur J Pharm Biopharm 2012; 82:598-604.
Rachid O, Rawas-Qalaji MM, Simons FE, Simons KJ. Epinephrine (adrenaline) absorption from new-generation, taste-masked sublingual tablets: a preclinical study. J Allergy Clin Immunol 2013; 131:236-8.
Liu Y, Sun C, Hao Y, Jiang T, Zheng L, Wang S. Mechanism of dissolution enhancement and bioavailability of poorly water soluble celecoxib by preparing stable amorphous nanoparticles. J Pharm Pharm Sci 2010; 13:589-606.
Ma Q, Sun H, Che E, Zheng X, Jiang T, Sun C, et al. Uniform nano-sized valsartan for dissolution and bioavailability enhancement: Influence of particle size and crystalline state. Int J Pharm 2013; 441:75-81.
Dali MM, Moench PA, Mathias NR, Stetsko PI, Heran CL, Smith Rl. A rabbit model for sublingual drug delivery: comparison with human pharmacokinetic studies of propranolol, verapamil and captopril. J Pharm Sci 2006; 95:37-44.
Ong CM, Heard CM. Permeation of quinine across sublingual mucosa, in vitro. Int J Pharm 2009; 366:58-64.
European Search Report for EP12842206 dated Mar. 31, 2015, 7 pages (national stage of PCT/US2012/61074 published as WO2013/59629).
Ting Qiao et al, Conjugation of catecholamines on magnetic nanoparticles coated with sulfonated chitosan, Colloids and Surfaces A: Physicochem, Eng. Aspects 380 (2011) 169-174.
Simons, Is epinephrine administration by sublingual table feasible for the first-aid treatment of anaphylaxes?, Biopharm Drup Dispos, Jul. 23, 2002 (5): 213-6, abstract.
International Preliminary Report on Patentability and Written Opinion for PCT/US13/45836 filed Jun. 14, 2013.
PubcheM: title: chemical and physical properties of epinephrine (only pertinent pages of 1 and 8), downloaded on Jun. 6, 2016, from http:/dav.uspto.gove/webappapplicationViewer.html?casenumber_14778887#).
Spyros Papiris, et al, Clinical Review: Severe Asthma, Critical Care. vol. 6(1), p. 30-44, published online Nov. 22, 2001.
Office Action dated Sep. 25, 2018 for U.S. Appl. No. 15/358,743.
Response filed Sep. 19, 2018 with European Patent Office for EP patent application No. 14 768 584.6.
Response filed Nov. 6, 2020, for U.S. Appl. No. 16/377,810.
Office Action For Canadian Patent Application No. 2,876,883, dated Nov. 19, 2020.
Office Action For Canadian Patent Application No. 2,907,770, dated Feb. 9, 2021.
For Canadian Patent Application No. 2,853,084, filed Oct. 19, 2012: Office Action dated Jun. 8, 2020 Response filed Oct. 6, 2020.
Response for EP Patent Application No. 14 768 584.6, filed Jul. 6, 2020.
Response to Final Office Action for U.S. Appl. No. 15/358,743, filed Jan. 16, 2020.
Response to Final Office Action for U.S. Appl. No. 16/377,810, filed Feb. 10, 2020.
Response to Office Action for U.S. Appl. No. 16/228,609, filed Mar. 9, 2020.
For U.S. Appl. No. 15/288,745: Restriction requirement dated Jul. 5, 2017; Response dated Sep. 5, 2017 Office Action dated Sep. 20, 2017; Response dated Jan. 22, 2018 Notice of Allowance and Interview Summary dated Feb. 27, 2018; Response and IDS dated May 29, 2018 (142 pages).
For U.S. Appl. No. 15/288,745: Office Action dated Jun. 8, 2018; IDS dated Jun. 11, 2018; Response and IDS dated Sep. 10, 2018; DS submitted Sep. 28, 2018 and Oct. 2, 2018; Notice of Allowance and interview summary dated Oct. 18, 2018 (85 pages).
For EP Application 14 768 584.6 (regional stage of PCT/US2014/31579): claim amendments dated May 12, 2016; second examiner's report dated May 28, 2018 (10 pages).
For EP Application 14 768 584.6 (regional stage of PCT/US2014/31579): European Search Report dated Aug. 10, 2016 (8 pages).
For U.S. Appl. No. 15/882,399: Office Action dated Mar. 22, 2018; Response dated Jun. 22, 2018 (24 pages).

(56) References Cited

OTHER PUBLICATIONS

Office Action for U.S. Appl. No. 15/358,743 dated Sep. 25, 2018.
Response for U.S. Appl. No. 15/358,743, filed Jan. 25, 2019.
Final Office Action for U.S. Appl. No. 15/882,399 dated Sep. 27, 2019.
RCE Response for US U.S. Appl. No. 15/882,399, filed Jan. 28, 2019.
For Canadian Patent Application No. 2,907,770, filed Mar. 24, 2014: Office Action dated Apr. 15, 2020 Response for filed Oct. 15, 2020.
Office Action for EP Patent Application No. 14 768 584.6, dated Sep. 26, 2019.
Office Action for U.S. Appl. No. 15/882,399 dated Mar. 29, 2019.
For U.S. Appl. No. 16/225,609: Office Action dated Sep. 23, 2020 (9 pages) Interview Summary dated Nov. 5, 2020 (4 pages) Response filed Feb. 23, 2021 (15 pages).
Office Action dated Feb. 9, 2021, for Canadian Patent App. No. 2853084 (3 pages).
Final Office Action dated Mar. 1, 2021, for U.S. Appl. No. 16/377,810.
Final Office Action dated Mar. 5, 2021, for U.S. Appl. No. 16/225,609.
International Search Report and Written Opinion for PCT/2019/056967 dated Dec. 23, 2019.
International Preliminary Report on Patentability and Written Opinion for PCT/2019/056967 dated Apr. 29, 2021.
Response to Office Action for U.S. Appl. No. 15/882,399, filed Jul. 26, 2019.
Office Action dated Mar. 16, 2018 for U.S. Appl. No. 15/358,743.
Response filed May 16, 2018 for U.S. Appl. No. 15/358,743.
Final Office Action for U.S. Appl. No. 16/225,609 dated Mar. 19, 2020.
Office Action for U.S. Appl. No. 16/377,810 dated May 13, 2020.
Response to Final Office Action for U.S. Appl. No. 15/358,743, filed Aug. 30, 2019.
European Search Report for EP Patent Application No. 13812628.9 dated Jul. 25, 2019.
Office Action for U.S. Appl. No. 15/358,743 dated Sep. 18, 2019.
For Canadian Patent Application No. 2,853,084: Office Action dated Oct. 25, 2018 (3 pages).
RCE response filed Jul. 1, 2021, for U.S. Appl. No. 16/377,810.
For Canadian Patent Application No. 2,853,084: Response filed Jun. 9, 2021.
Schianti et al, Rifampicin Nanoprecipitation using Flow Focusing Microfuidic Device, J of Nanomedicine and Nanotechnology, 2013, 6 pages.
Examination Report for European Patent Application No. 12842206.0, dated Apr. 9, 2020.
Response filed Apr. 24, 2019 for Canadian Patent Application No. 2,853,084.
International Search Report and Written Opinion for PCT/2019/056967 dated Dec. 23, 2019.
Final Office Action for U.S. Appl. No. 15/262,961 dated Jul. 24, 2018.
Response for U.S. Appl. No. 15/262,961, filed Oct. 9, 2018.
International Search Report and Written Opinion for International Application No. PCT/US19/56967; dated Dec. 23, 2019.
International Preliminary Report on Patentability (IPRP) for International Application No. PCT/US19/56967; dated Apr. 29, 2021.
Issue Notice dated Jan. 5, 2022 for U.S. Appl. No. 16/225,609.

* cited by examiner

SUBLINGUAL EPINEPHRINE COMPOSITIONS INCLUDING PH-MODIFYING EXCIPIENTS AND PENETRATION ENHANCERS AND METHODS FOR USE THEREOF

FIELD OF THE INVENTION

The invention is encompassed within the field of drug formulation and generally relates to modifications in drug formulation that result in improved delivery of sublingually-administered medication, particularly to modifications in drug formulation that enhance permeability of the active ingredient of the sublingually-administered medication, and most particularly to sublingual epinephrine compositions including epinephrine fine particles formulated with pH-modifying excipients and penetration enhancers that improve sublingual delivery/absorption of epinephrine.

BACKGROUND

Epinephrine (Epi) is the drug of choice for the emergency treatment of anaphylaxis (1-4). For out-of-hospital emergency treatment of anaphylaxis. Epi auto-injectors such as EpiPen3®, EpiPen Jr® (Mylan Specialty L.P, Basking Ridge, NJ. USA) are prescribed. However, self-injectable Epi is underutilized when anaphylaxis occurs (5,6). The drawbacks of Epi auto-injectors include: high cost which limits affordability and availability worldwide (6), bulkiness, limitations if repeat dosing is required (7), fear and anxiety associated with the use of needles, and dosing errors due to incorrect administration technique (8).

Epinephrine is extensively metabolized after oral administration by the catechol-O-methyltransferase in the gastrointestinal tract and by monoamine oxidase in the gastrointestinal tract and in the liver (9), in aqueous solutions, Epi is unstable in the presence of light, oxygen, heat, and neutral or alkaline pH values. Epi decomposes into neurotoxin molecules, adrenochrome, and adrenolutin (10).

The sublingual route of administration is a promising alternative route for Epi administration. Drugs that can be absorbed sublingually bypass potential metabolic conversion in the gastrointestinal tract and hepatic first-pass metabolism and reach the systemic circulation in a pharmacologically-active form (11-14). The high vascularity of the sublingual mucosa and the low molecular weight of Epi facilitate its rapid absorption directly into the venous circulation.

Orally-disintegrating tablets, which disintegrate rapidly in the minimal volume of the oral saliva, are good candidate for the sublingual administration of Epi (15, 16). They would release Epi instantly into the sublingual cavity to be rapidly absorbed through the sublingual mucosa into the systemic circulation (17).

The optimal pH values for the stability of Epi in aqueous solution are 3.0-3.8 (10). However, the pH of the saliva under normal conditions varies between 5.8 to 7.1. Also, some pharmaceutical excipients and acidic or alkaline drinks may alter the normal saliva pH, which may affect the stability of sublingually administered Epi (18).

The administered sublingual tablets are recommended to be kept under the patient's tongue until it is completely disintegrated or dissolved and can no longer be felt under the tongue. The time for the complete tablet disintegration or dissolution under the patient's tongue should not be more than 2 to 5 minutes and patients are instructed not to cat or drink anything during this time. The required therapeutic dose of the administered drug should be already absorbed during this time into the systemic circulation through the sublingual mucosa. Although the contact time between Epi and saliva in the sublingual cavity will be for a short period of time, there is no evidence in the literature that indicates Epi will be stable during its sublingual administration and how fluctuations in the saliva pH may affect its stability. Therefore, it is very crucial to evaluate how the change in the saliva pH due to various drinks and potential pharmaceutical excipients used in the tablet formulation would affect the stability of Epi during its sublingual administration. Furthermore, the stability of Epi in human saliva during its sublingual administration needs to be evaluated for any potential enzymatic degradation of Epi that may take place during its sublingual administration and to assess the feasibility of using the sublingual route as a potential route for the administration of Epi for the first-aid treatment of anaphylaxis.

Also, the permeability of drugs depends on their degree of ionization at the site of administration (19). The degree of ionization of weak basic or acidic drugs is based on prevailing pH. pH-modifying excipients incorporated into the dosage form can alter absorption medium's, therefor, can affect the permeability and bioavailability of administered drugs. The selection of excipients to be used in a dosage form depends on the properties of the target absorption site. The addition of pH modifiers into a tablet formulation designed for sublingual administration ensures that the pH of the saliva at the absorption site is controlled within the range that is optimal for drug absorption and reduces absorption's variabilities due to individual saliva pH variability, or due to any potential effect of food and drinks on saliva pH. The selection of these excipients is particularly important for Epi as a weak base. Its extent of absorption can be greatly dependent on its degree of ionization, which is mainly affected by the pH of the saliva. Therefore, the evaluation of various pH-modifying excipients is critical for enhancing Epi sublingual permeability and absorption, therefore, its bioavailability.

Another approach to enhance drug absorption is use of penetration (permeability) enhancers. There is a wide range of enhancers that have been evaluated at various concentrations for their ability to enhance drug absorption and for their safety (20). The mechanism of permeation enhancement can be utilized for hydrophilic and lipophilic drugs through paracellular diffusion, transcellular diffusion, or both. Epi has log P of −1.37 (21), which can be a candidate for using a penetration enhancer to increase it absorption. Previous studies have shown that the relative sublingual bioavailability of Epi is low when compared to the intramuscular injection of Epi (22). Therefore, the assessment of various penetration enhancers to be incorporated into the dosage form to be administered sublingually on Epi sublingual permeability is needed. A wide range of permeation enhancers can be used at various concentrations to enhance Epi permeability. For example, sodium dodecyl sulfate (SDS) can be used at concentration that ranges from 0.05% to 1% (23, 24) and palmitoyl carnitine chloride (PCC) can be used at concentration that ranges from 0.05 mM to 0.35 mM (25, 26) with minimal and revisable local tissue damage (27).

Without being bound by theory, it is thought that fabrication of epinephrine into fine particles, including epinephrine nanoparticles or nanocrystals and epinephrine microparticles or microcrystals, and incorporation of the epinephrine line particles into a tablet formulation with pH-modifying excipients and penetration enhancers wilt significantly increase the permeability of epinephrine and thus will significantly increase the absorption of the sublingually-administered epinephrine resulting with reduction of sublingual epinephrine dose required for both adults and children.

Epinephrine is an important medication in health systems worldwide for management of life-threatening allergies, i.e. anaphylaxis, cardiac events, i.e. cardiac arrest, and breathing difficulties, i.e. asthma, bronchial asthma, bronchitis, emphysema, and respiratory infections. It would be very advantageous to have non-invasive sublingual drug delivery of epinephrine as a potential alternative, patient-friendly, convenient, and cost-effective dosage form.

SUMMARY OF THE INVENTION

Epinephrine (Epi) is life-saving in the treatment of anaphylaxis. In community settings, a first-aid dose of epinephrine in an amount of 0.1 mg, 0.15 mg, or 0.3 tug is injected into the mid-outer thigh by patients or caregivers using an auto-injector such as an EpiPen® (epinephrine auto-injector 0.3 or 0.15 mg, Mylan Inc., Basking Ridge, NJ) or Auvi-Q® (epinephrine auto-injector 0.1, 0.3, or 0.15 mg, kaleo, Inc., Richmond, VA). Epi auto-injectors are under-used because of needle phobia, bulky size, and high cost; additionally, there are only two to three fixed doses, shelf-life is only 12-18 months, and unintentional injection and injury sometimes occur.

The instant invention circumvents the aforementioned problems by providing a fast-disintegrating epinephrine tablet formulation for anaphylaxis treatment. Although this formulation was designed with regard to anaphylaxis, it is equally effective and contemplated for use in treatment of any condition responsive to epinephrine such as cardiac events, i.e. cardiac arrest, and breathing difficulties, i.e. asthma, bronchial asthma, bronchitis, emphysema, and respiratory infections.

In a validated rabbit model, this fast-disintegrating epinephrine tablet formulation resulted in plasma epinephrine concentrations similar to those achieved after a 0.3 mg epinephrine intra-muscular injection. (22) Furthermore, epinephrine was stable in these fast-disintegrating tablets for at least seven years.

The instant inventor hypothesized that adjusting the pH of the sublingual microenvironment that surrounds Epi tablet using alkalizing excipient can modify the pH of the saliva in that area (tablet's diffusional layer or the stagnant unstirred layer that forms around the tablet and contains the dissolved Epi from the tablet) and reduce Epi ionization without affecting its stability, which will increase Epi permeability. Also, incorporating a penetration enhancer in the sublingual tablet formulation can increase Epi permeability as well. Some experiments, which led to the inventive compositions, are described herein: 1) evaluate the stability of Epi in various media, 2) evaluate the effect of modifying the pH of the diffusion medium on enhancing Epi sublingual permeability, 3) evaluate the ability of pH-modifying excipients to alter the microenvironment's pH of the absorption medium of Epi tablet, and 4) evaluate the effect of using various penetration enhancers on enhancing Epi sublingual permeability.

One of the most common approaches to enhance the rate of drug dissolution and absorption is to significantly reduce its particle size to the micro- or nano-size range. Drug nanocrystals (NC) or microcrystals (MC) are advantageous due to the minimal required excipients and almost 100% of the pure drug is produced during the fabrication process (28). Also, the collected dried drug NC or MC can be formulated into various dosage forms.

The phrase "epinephrine fine particles" refers to epinephrine particles of about 2.5 nm or less to about 500 nm-100 nm in size and includes epinephrine nanoparticles or nanocrystals and epinephrine microparticles or microcrystals.

In one aspect, the invention provides epinephrine fine particles.

In one aspect, the invention provides epinephrine nanoparticles. The epinephrine can be either an epinephrine base, epinephrine bitartrate salt or other effective epinephrine salt, or prodrug of epinephrine.

In another aspect, the invention provides epinephrine nanocrystals. A nanocrystal is a nanoparticle having a crystalline structure. The term "nanocrystal" is a more specific term for describing a nanoparticle. A drug nanocrystal contains almost 100% pure drug, thus an epinephrine nanocrystal contains almost 100% pure epinephrine. A drug nanoparticle can include nanocrystals or a drug encapsulated within a polymer at different ratios. One example is the epinephrine nanoparticles comprising chitosan and tripotyphosphate (TPP) described in the previously-filed related application; U.S. Provisional Patent Application Ser. No. 61/550,359, filed on Oct. 21, 2011.

The term "about" as used in this application refers to a quantity at or near a defined quantity which will still allow for desired function.

In a further aspect, the invention provides improvements in delivery of sublingually-administered medication, particularly, but not limited to, enhancing permeability of the active ingredient of the sublingually-administered medication.

In an embodiment, the invention provides sublingual epinephrine compositions including epinephrine fine particles formulated with pH-modifying excipients and penetration enhancers.

In one aspect of this embodiment, the invention encompasses a sublingual composition formulated as a fast-disintegrating tablet. This composition includes epinephrine fine particles, for example, but not limited to epinephrine bitartrate fine particles, and one or both of a pH-modifying excipient and a penetration enhancer. A preferred, non-limiting epinephrine is epinephrine bitartrate equivalent to about 20 mg or less epinephrine, 15 mg or less epinephrine, or preferably ranging from about 20 mg to about 1 mg epinephrine. Non-limiting examples of a pH-modifying excipients are the alkalizing agents, sodium carbonate, sodium bicarbonate, and calcium citrate. These alkalizing agents can be added in any effective percentage to the inventive compositions, for example, but not limited to sodium bicarbonate added at a percentage of 0.75% w/w or 10% w/w of tablet weight. Non-limiting examples of penetration enhancers are sodium dodecyl sulfate (SDS) or palmitoyl carnitine chloride (PCC). These penetration enhancers can be added in any effective percentage to the inventive compositions, for example, but not limited to SDS added at 0.075% w/v or 1% w/w of API used and PCC added at 1.2% w/v or 16% w/w of API used.

In yet another aspect, the invention provides methods for controlling the microenvironment at the site of drug delivery in an oral cavity. For example, the invention provides a method for controlling pH of saliva within a range optimal, preferred, but not limited to a range of about 6.8 and about 8, for absorption at a site of sublingual administration in a subject in need thereof. In another similar aspect, the invention provides a method for altering ionization of epinephrine at a site of sublingual administration of the epinephrine in a subject in need thereof. Both methods include providing a composition including epinephrine fine particles and at least one of a pH-modifying excipient and a penetration enhancer, and administering the composition to the subject. Control of the pH of saliva preferably includes increasing the pH.

In another aspect, the invention provides a composition including epinephrine nanoparticles or nanocrystals capable of enhancing the sublingual bioavailability of epinephrine for the emergency treatment of anaphylaxis and/or other conditions responsive to epinephrine.

In another aspect, the invention provides "oral disintegrating tablets (ODTs)" including epinephrine nanoparticles or nanocrystals or epinephrine microparticles or microcrystals.

As described herein, buccal or sublingual oral disintegrating tablets (ODTs) are distinguished from conventional sublingual tablets, lozenges, or buccal tablets by the ODTs' ability to fully dissolve or disintegrate in less than about one minute in the mouth.

The invention also provides pharmaceutical compositions including epinephrine nanoparticles or nanocrystals or epinephrine microparticles or microcrystals in ODT form.

The invention also provides a pharmaceutical composition including epinephrine nanoparticles or nanocrystals or epinephrine microparticles or microcrystals and a pharmaceutically-acceptable carrier for buccal or sublingual administration.

The phrase "pharmaceutically-acceptable carrier" refers to an inactive and non-toxic substance used in association with an active substance, i.e. epinephrine, especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (NMIs).

The invention also provides a pharmaceutical composition, for buccal or sublingual administration, including epinephrine nanoparticles or nanocrystals or epinephrine microparticles or microcrystals and at least one of a pharmaceutically-acceptable carrier, a surfactant, a penetration enhancer, a pH-modifying excipient, and a mucoadhesive. The pharmaceutical composition can further include at least one of a taste enhancer and a sweetening agent and mouth-feel enhancer. A non-limiting example of a taste enhancer is citric acid. Citric acid masks the bitter taste of epinephrine. A non-limiting example of a sweetening agent and mouth-feel enhancer is mannitol. The pharmaceutical composition can further include at least one of a filler, a lubricant, and a disintegrant. Non-limiting examples include microcrystalline cellulose (filler), magnesium stearate (lubricant), and low-hydroxypropyl ethers of cellulose (disintegrant).

Additionally, the invention provides a pharmaceutical composition including epinephrine nanoparticles or nanocrystals or epinephrine microparticles or microcrystals, in which the bitter taste of the epinephrine is masked by a taste enhancer. A non-limiting example of a taste enhancer is citric acid.

In another aspect, the invention provides a method for enhancing sublingual bioavailability of epinephrine in a subject in need thereof including steps for providing a composition including epinephrine nanoparticles or nanocrystals or epinephrine microparticles or microcrystals and at least one pharmaceutically-acceptable carrier and administering the composition to the subject. The described fast-disintegrating epinephrine tablets enhance bioavailability of epinephrine by releasing epinephrine within sixty seconds of administration. The term "subject" includes any human being or animal that can benefit from the inventive compositions and methods. The term "patient" is also used herein to refer to the subject.

In another aspect, the invention provides a method for treating a condition responsive to epinephrine in a subject in need thereof including steps for providing a composition including epinephrine nanoparticles or nanocrystals or epinephrine microparticles or microcrystals and at least one pharmaceutically-acceptable carrier and administering the composition to the subject. Conditions responsive to epinephrine react to administration of epinephrine. Non-limiting examples of conditions responsive to epinephrine include a cardiac event, i.e. cardiac arrest, or an allergic reaction, i.e. anaphylaxis, asthma, or bronchial asthma.

The phrase "effective amount" refers to the amount of a composition necessary to achieve the composition's intended function.

The phrase "pharmaceutically-effective dose" refers to the amount of a composition necessary to achieve a desired pharmaceutical effect. It is often desirable to use the smallest effective dose of a drug. One example of a dose range for the described epinephrine nanoparticles or nanocrystals or epinephrine microparticles or microcrystals is approximately 1 mg to 40 mg epinephrine nanoparticles or nanocrystals or epinephrine microparticles or microcrystals.

The phase "therapeutically-effective amount" refers to the amount of a composition required to achieve the desired function, i.e. treatment of the condition responsive to epinephrine.

In another aspect, the invention provides a method for treating a breathing difficulty in a subject in need thereof including steps for providing a composition including epinephrine nanoparticles or nanocrystals or epinephrine microparticles or microcrystals and at least one pharmaceutically-acceptable carrier and administering the composition to the subject. Breathing difficulties responsive to epinephrine include, but are not limited to, breathing difficulties associated with anaphylaxis, asthma, bronchial asthma, bronchitis, emphysema, and respiratory infections.

The invention additionally provides a method for treatment of an allergic emergency in a subject diagnosed with or suspected of having an allergic emergency including steps for providing a composition including epinephrine nanoparticles or nanocrystals or epinephrine microparticles or microcrystals and at least one pharmaceutically-acceptable carrier and administering the composition to the subject. Non-limiting examples of allergic emergencies are anaphylaxis, asthma, and bronchial asthma.

In an additional aspect, the invention provides a method for treatment of a cardiac event in a subject diagnosed with or suspected of having a cardiac event including steps for providing a composition including epinephrine nanoparticles or nanocrystals or epinephrine microparticles or microcrystals and at least one pharmaceutically-acceptable carrier and administering the composition to the subject. A non-limiting example of a cardiac event is cardiac arrest.

Any of the above-described epinephrine fine particles (including epinephrine nanoparticles or nanocrystals and epinephrine microparticles or microcrystals), compositions, and pharmaceutical compositions can be formulated for buccal or sublingual administration, particularly those epinephrine fine particles (including epinephrine nanoparticles or nanocrystals and epinephrine microparticles or microcrystals), compositions, and pharmaceutical compositions intended for use in emergency situations.

In another aspect, any of the above-described epinephrine fine particles (including epinephrine nanoparticles or nanocrystals and epinephrine microparticles or microcrystals) can be used in the manufacture of any of the above-described compositions and pharmaceutical compositions.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

Figure 1:
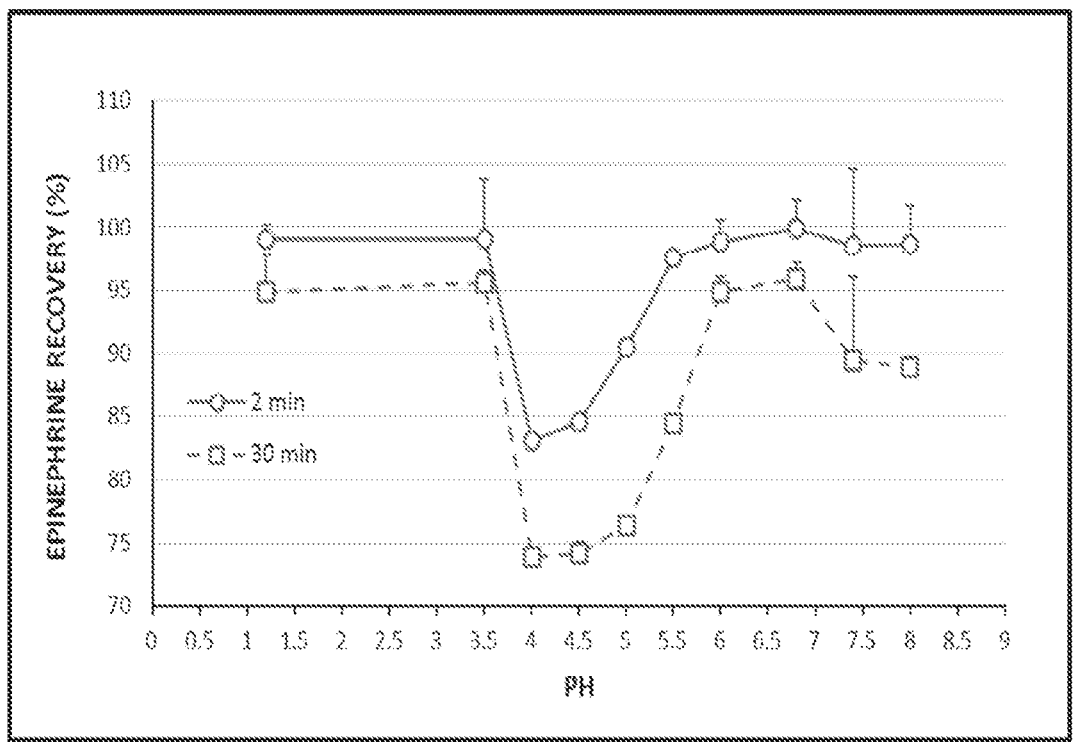
FIG. 1 is a graph illustrating epinephrine recovery (%) in various pH level, Mean±SD (n=3).

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions, formulations, epinephrine fine particles, methods, procedures, and techniques described herein along with any further application of the principles of the invention as described herein, are contemplated as would normally occur to one skilled in the art to which the invention relates.

As noted above, the experiments described herein had defined objectives leading to development of the inventive compositions.

First, the short-teen stability of epinephrine (Epi) at wide range of pH was assessed. Modification of the pH of the absorption's microenvironment can alter the degree of drug ionization and therefore its permeability. Altering the saliva pH (5.5-7.2) in order to enhance Epi sublingual absorption and reduce its absorption variability can, on the other hand, negatively affect its stability. It was thought that altering Epi ionization by modifying the pH of absorption medium, without negatively affecting Epi stability, can enhance Epi permeability and optimize sublingual Epi delivery as an alternative route for the treatment for anaphylaxis and other conditions responsive to Epi.

Epi was found to be relatively stable for the time-period required for its sublingual administration at the saliva pH and up to pH 8. Altering the pH of the absorption's microenvironment up to pH 8 to enhance Epi sublingual delivery and reduce its absorption variability should not affect its stability.

Next, the effect of modifying the pH on the sublingual permeability of epinephrine (Epi) in order to alter its degree of ionization was evaluated. It was thought that altering Epi ionization by modifying the pH of absorption medium can enhance Epi permeability and optimize sublingual Epi delivery as an alternative route for the treatment for anaphylaxis and other conditions responsive to Epi.

It was found that increasing the pH of the diffusion medium and the subsequent reduction in Epi ionization can result in a significant increase in the Epi sublingual permeation.

Finally, the effect of different permeability enhancers on the sublingual permeability of epinephrine (Epi) was evaluated. It was thought that the incorporation of a permeability enhancer can further enhance Epi sublingual permeability as a potential alternative route of administration for the treatment of anaphylaxis and other conditions responsive to Epi.

It was found that penetration enhancers were able to enhance the sublingual permeability of Epi. Sodium dodecyl sulfate (SDS) was superior to palmitoyl carnitine chloride (PCC) in enhancing the sublingual permeation of Epi. The incorporation of a permeability enhancer into Epi formulation can significantly enhance the permeability and potentially the sublingual absorption of Epi as a potential alternative route of administration for the treatment of anaphylaxis and other conditions responsive to Epi.

Example 1: Stability of Epinephrine (Epi) in Various Media

Epi optimal stability in aqueous solution is at pH range of 3.0.3.8 (10). However, the normal saliva pH is between 5.4-7.1, which can be also altered due to food, drinks, or excipients used in the sublingual dosage form. pH-modifying excipients can be used in the sublingual formulation to alter the degree of drug ionization and therefore its permeability. However, modifying the saliva pH using pH-modifying excipients in order to enhance Epi sublingual absorption and/or reduce its absorption variability due to food or drinks can, on the other hand, negatively affect its stability. Therefore, the short-term stability, 20-30 min, of Epi was evaluated in various media to test the feasibility of Epi sublingual administration at various pH values for the treatment for anaphylaxis and other conditions responsive to Epi.

Stability of Epinephrine in Various pH

Epinephrine bitartrate (EpiBit) equivalent to 20 mg Epi was dissolved in 2 mL of Mcvilian buffer (n=3) (phosphate acetate buffer) at specific pH including pH 1.2, 3.5, 4.5, 5, 5.5, 6, 6.8, 7.4, and 8. Aliquot samples were withdrawn at specific time intervals including 2 (maximum expected time for sublingual administration), 4, 6, 10, 15, and 30 min. Withdrawn samples were immediately diluted with a stabilizing solution containing 0.1 M perchloric acid and 0.1 mM sodium metabisulfite to stabilize and stop any potential epi degradation. Collected samples were frozen for further analysis by HPLC for Epi content using the USP method for Epi injection. Epi recovery % at $T_0$ was used as a positive control for each sample. The mean±SD of Epi recovery (%) in each pH at different time were calculated and statistically compared using repeated measures-ANOVA and Tukey-Kramer Tests (p<0.05).

The mean±SD (n=3) Epi recovery (4%1 at the different time intervals in the various pH tested are shown in Table 1. Mean±SD (n=3, Epi recovery (%) was not significantly different (p>0.05) from the original concentration (positive control $T_0$) at the different sampling time intervals in pH range from 1.2 to 3.5 and 5.5 to 8 (FIG. 1). At pH 4.4.5 and 5 Epi recovery (%) declined significantly (p<0.05).

TABLE 2

Mean ± SD (n = 3) epinephrine stability in Human Saliva

| Time (min) | Epi Recovery (%) Saliva |
|---|---|
| 0 | 100 ± 0.2 |
| 2 | 96 ± 0.2 |
| 4 | 96 ± 0.2 |
| 6 | 95 ± 0.1 |
| 10 | 95 ± 0.2 |
| 15 | 92 ± 0.2* |
| 30 | 84 ± 0.0* |

*p < 0.05 from $T_0$

TABLE 1

Mean ± SD (n = 3) epinephrine stability in various pH
Epi Recovery (%)

| Tims (min) | pH 1.2 | pH 3.5 | pH 4.0 | pH 4.5 | pH 5 | pH 5.6 | pH 6 | pH 6.8 | pH 7.4 | pH 8 |
|---|---|---|---|---|---|---|---|---|---|---|
| 0 | 100 ± 4 | 100 ± 4 | 100 ± 0 | 100 ± 0 | 100 ± 0 | 100 ± 0 | 100 ± 3 | 100 ± 2 | 100 ± 5 | 100 ± 3 |
| 2 | 99 ± 1 | 99 ± 5 | 85 ± 0.3* | 85 ± 0.7 | 90 ± 0.0* | 98 ± 0.0 | 99 ± 2 | 100 ± 2 | 99 ± 6 | 99 ± 3 |
| 4 | 100 ± 3 | 99 ± 5 | 82 ± 0.2* | 84 ± 0.7* | 98 ± 0.0* | 97 ± 0.0 | 99 ± 2 | 99 ± 2 | 98 ± 6 | 98 ± 3 |
| 8 | 95 ± 4 | 98 ± 5 | 92 ± 0.2* | 82 ± 0.9* | 97 ± 0.0* | 97 ± 0.0 | 98 ± 2 | 98 ± 2 | 95 ± 6 | 95 ± 4 |
| 10 | 96 ± 2 | 96 ± 4 | 80 ± 0.5* | 80 ± 0.7* | 86 ± 0.0* | 96 ± 0.1 | 100 ± 2 | 98 ± 2 | 94 ± 8 | 94 ± 2 |
| 15 | 95 ± 2 | 96 ± 3 | 79 ± 0.6* | 78 ± 0.7* | 84 ± 0.1* | 88 ± 0.1 | 97 ± 3 | 97 ± 2 | 93 ± 8 | 91 ± 3* |
| 30 | 95 ± 3 | 96 ± 1 | 74 ± 0.7* | 74 ± 0.8* | 76 ± 0.0* | 84 ± 0.0* | 95 ± 1 | 96 ± 1 | 89 ± 7 | 89 ± 1* |

*p < 0.05 from $T_0$

Epi was stable in a wide range of pH values for sufficient time to allow for sublingual drug administration except between pH 4 to 5, which resulted in 10-17% Epi loss in the first 2 min. Epi sublingual administration should be feasible and would have minimal or no degradation due to incorporating pH-modifying excipients into the tablet formulation or due to human consumption of various drinks with wide range of acidity and alkalinity (except between pH 4 to 5) without adjusting the pH.

Stability of Epinephrine in Human Saliva Saliva samples were collected from human volunteer. The volunteer was asked not to eat or drink any acidic, alkaline, or spicy food or beverages and to rinse his mouth before the collection of saliva. The saliva was collected into an ice-bathed beaker and then degased to remove air bubbles and then filtered through 0.45 μm membrane.

EpiBit equivalent to 2 mg Epi was dissolved in 400111 (equivalent to 10 mg Epi in 2 mL) of saliva (n=3) that was immersed into 37° C. water bath for 30 minutes before the start of the testing study. Aliquot samples were withdrawn at specific time intervals including 2, 4, 6, 10, 15, and 30 min. Withdrawn samples were immediately diluted with Epi stabilizing solution containing 0.1 M perchloric acid and 0.1 mM sodium metabisulfite to stabilize and stop any potential epi degradation. Collected samples were frozen for further analysis by HPLC for Epi content using the USP method for Epi injection. The mean±SD of Epi recovery (%) was calculated.

Figure 2:
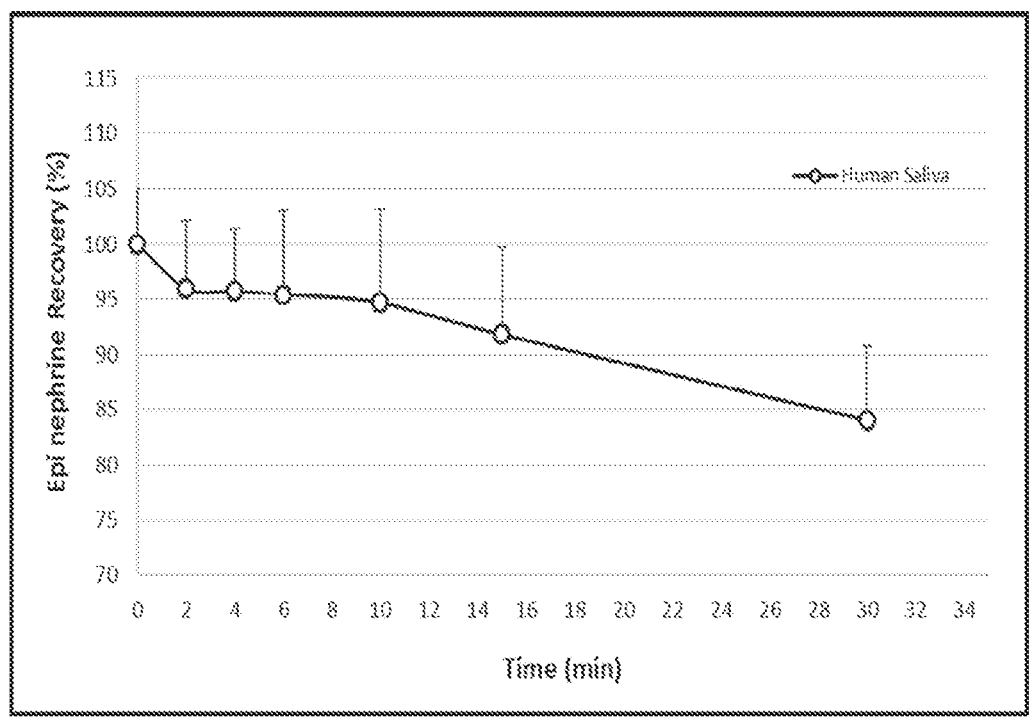
FIG. 2 is a graph illustrating epinephrine recovery (%) in human saliva, Mean±SD (n=3).

The mean±SD (n=3) Epi recovery (%) at the different time intervals in human saliva were shown in Table 2 and FIG. 2.

Epi was stable in human saliva (saliva pH and up to pH 8) for sufficient time to allow for sublingual drug administration. Epi concentration was only significantly lower than the initial concentration in human saliva after 15 and 30 min (92±0.2% and 84±0.0%, respectively). Epi is suitable for sublingual administration and would have minimal or no significant degradation due to human saliva's pH and composition. Altering the pH of the absorption microenvironment up to pH 8 to enhance Epi sublingual delivery and reduce its absorption variability should not effect stability.

Example 2: Epinephrine Sublingual Permeability in Various pH

Modification of the pH of the absorption's microenvironment due to food, drinks, or individual saliva variability can cause variability in drug permeability and absorption due to altering its degree of drug ionization. Also, pH-modifying excipients can be incorporated in the sublingual formulation to reduce drug ionization and therefore enhance its permeability and absorption. Therefore, the sublingual permeability of Epi at a wide range of pH was evaluated in order to determine the pH values at which Epi permeability is optimal.

Excising and Preparing Porcine Sublingual Mucosa

Frozen pig's heads were obtained from local abattoir. Then, they were defrosted at room temperature. The porcine mucosa were excised by dissecting the sublingual mucosa and removing the underlying connective tissue using a scalpel and fine tweezers using established surgical techniques. The excised mucosa were frozen on aluminum foil at −20° C. until used (<4 weeks).

Epinephrine Permeability Studies

Static vertical jacketed Franz Cells with 01) of 20 mm and reservoir volume 20±1 mL (PermeGear Inc., Hellertown, PA) were used to measure the permeability of Epi at various pH. The sublingual mucosa (floor of the mouth) excised from pigs were used as the diffusion membranes. Mcvilian buffer at various pH was used in the donor cell as a diffusion medium.

Before each experiment, the mucosal membranes were defrosted at room temperature and mounted between the donor and receptor chambers and clamped using a metal clamp. The receptor chamber that has a magnetic stirrer was filled with the diffusion medium before mounting the membranes and air bubbles were removed after mounting the membranes and before the experiment. The water bath was set at 37° C. for the circulating water in the jacketed Franz Cells. The mounted membranes were equilibrated with the diffusion medium for 30 min from both sides before the experiment and were checked for any leaks.

EpiBit equivalent to 20 mg Epi was dissolved in 2 mL of Mcvilian buffer (n=4) at specific pH including pH 5, 6, 6.8, 7.4, and 8.

Aliquots were withdrawn from the receptor chamber using 6 inch-long needles (Popper & Sons. Inc, New Hyde Park, NYC) and 1 mL syringes at 5, 10, 15, 20, 30, 45, 60, 75, and 90 min. The withdrawn volumes were replaced with fresh medium.

Samples were transferred to HPLC vials for HPLC analysis according to USP Method.

The cumulative amount of the Epi permeated over time ($AUC_{0-90min}$, μg/cm$^2$/min), influx (J, μg/cm$^2$/min), and permeability coefficient (P, cm/min) were calculated and statistically compared using ANOVA and Tukey-Kramer Tests.

Figure 3:
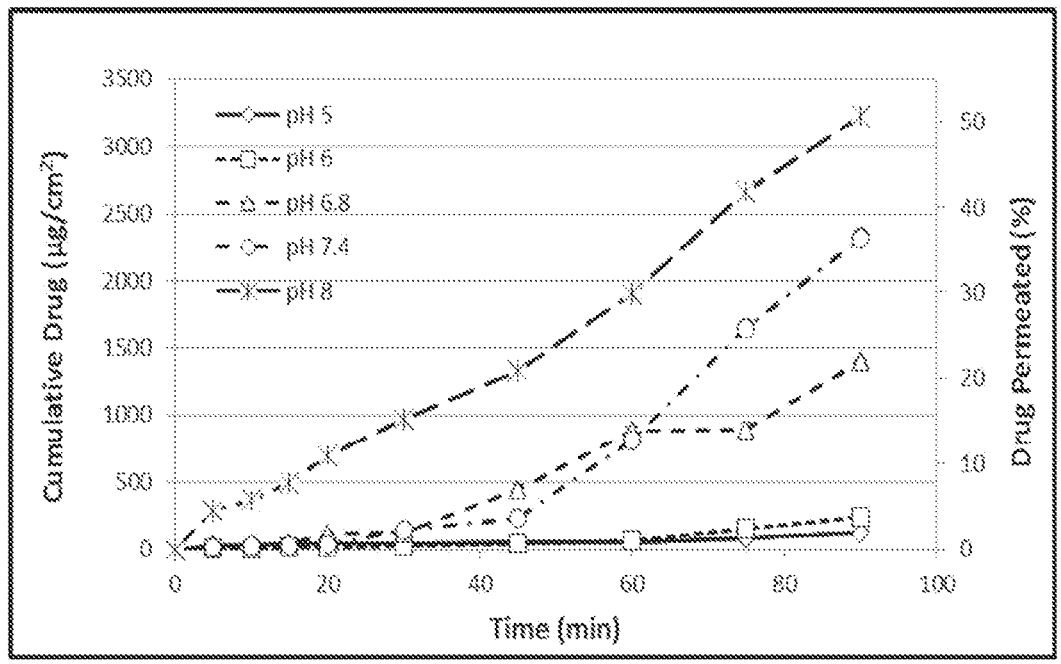
FIG. 3 is a graph illustrating cumulative permeated epinephrine and percentage through porcine sublingual mucosa over time at various pH, Mean±SD (n=4).

The mean±SD (n=4) cumulative diffused Epi per area at various pH were presented in Table 3 and FIG. 3. The Mean percentage of diffused Epi per area at various pH were presented in Table 4 and FIG. 3.

Figure 4:
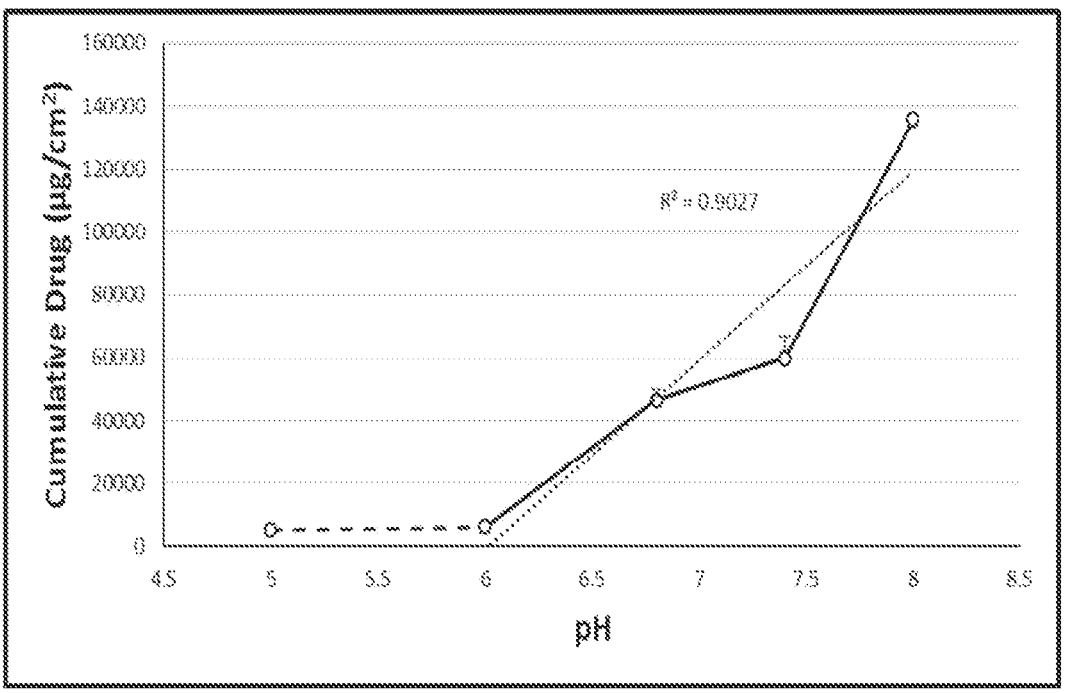
FIG. 4 is a graph illustrating $AUC_{0-90}$ of permeated epinephrine through porcine sublingual mucosa at various pH, Mean±SD (n=4).
Figure 5:
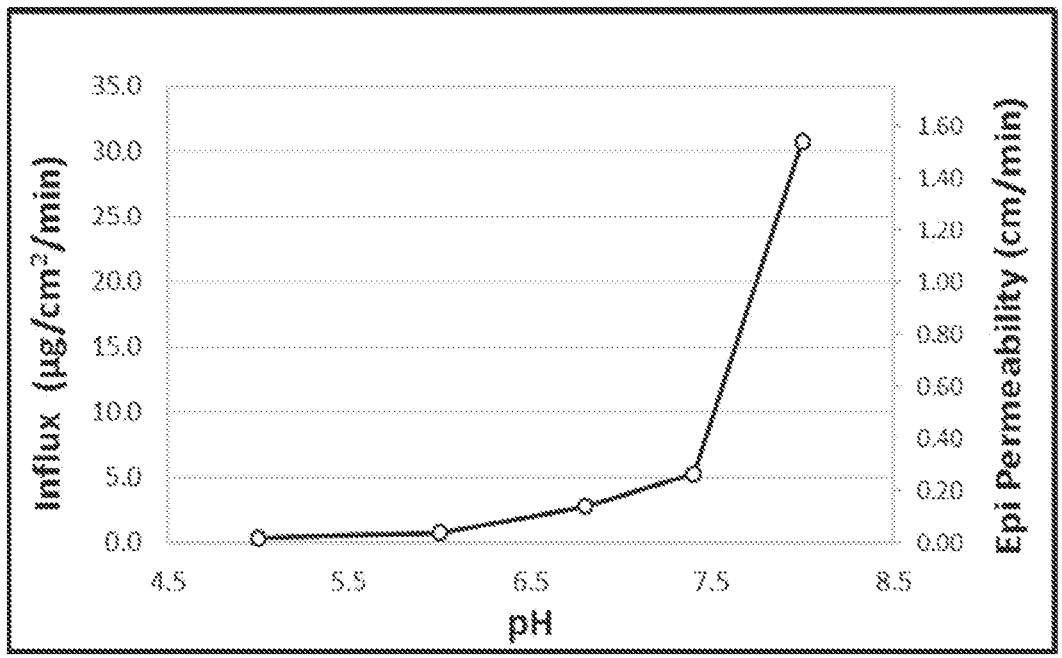
FIG. 5 is a graph illustrating epinephrine influx and permeability through porcine sublingual mucosa at various pH, Mean±SD (n=4).

The mean (±SD) Epi $AUC_{0-90min}$, J, P were presented in Table 5. Also, Epi $AUC_{0-90min}$, influx (J) and permeability (P) at each pH were illustrated in FIGS. 4 and 5. $AUC_{0-90}$, J, P at the various pH were significantly different ($p<0.05$) from each other except at pH 5 and 6, which were not significantly different from each other but. Epi $AUC_{0-90min}$ increased linearly ($R^2=0.9$) as the pH was increase from 6 to K. At pH 8 Epi sublingual permeability was increased about 11-fold compared to at pH 6.8, which is the average pH of human saliva.

pH had a significant effect on Epi sublingual permeability. As the pH was increased, the degree of ionization was decreased and result in increasing the sublingual permeation of Epi.

Increasing the pH of the diffusion medium and the subsequent reduction in Epi ionization can result in a significant increase in the Epi sublingual permeation.

TABLE 3

Mean ± SD (n = 4) cumulative permeated epinephrine (20 mg) per area (μg/cm$^2$) through porcine sublingual mucosa at various pH.

| Time (min) | pH 5 | pH 6 | pH 6.6 | pH 7.4 | pH 8 |
|---|---|---|---|---|---|
| 5 | 33.8 ± 1.8 | 4.7 ± 1.5 | 20.2 ± 1.2 | 18.1 ± 0.7 | 283.6 ± 1.7 |
| 10 | 37.5 ± 0.6 | 7.7 ± 1.6 | 27.6 ± 0.4 | 22.2 ± 1.3 | 367.9 ± 3.0 |
| 15 | 40.3 ± 1.3 | 11.6 ± 1.0 | 44.9 ± 3.0 | 29.2 ± 1.1 | 491.3 ± 9.3 |
| 20 | 43.6 ± 1.1 | 15.7 ± 3.3 | 115.3 ± 2.6 | 33.1 ± 0.6 | 700.0 ± 7.0 |
| 30 | 46.7 ± 1.4 | 23.2 ± 6.0 | 119.9 ± 2.9 | 145.8 ± 3.8 | 967.0 ± 14.4 |
| 45 | 50.7 ± 1.5 | 43.3 ± 15.5 | 447.5 ± 212.7 | 232.4 ± 6.6 | 1325.7 ± 11.7 |
| 60 | 58.7 ± 3.9 | 66.4 ± 3.6 | 877.6 ± 24 | 810.2 ± 156.9 | 1902.2 ± 19.1 |
| 75 | 78.2 ± 7.5 | 147.8 ± 41.1 | 889.7 ± 3.2 | 1644.8 ± 317.7 | 2667.9 ± 30.7 |
| 90 | 118.1 ± 3.5 | 240.0 ± 68.5 | 1401.5 ± 85.0 | 2316.0 ± 4.6 | 3226.6 ± 29.9 |

TABLEs 4

Mean ± SD (n = 4) percentage of diffused epinephrine (%) through porcine sublingual mucosa at various pH.

| Time (min) | pH 5 | pH 6 | pH 6.8 | pH 7.4 | pH 8 |
|---|---|---|---|---|---|
| 5 | 0.5 ± 0.03 | 0.1 ± 0.02 | 0.3 ± 0.02 | 0.3 ± 0.01 | 4.5 ± 0.03 |
| 10 | 0.6 ± 0.01 | 0.1 ± 0.02 | 0.4 ± 0.01 | 0.3 ± 0.02 | 5.8 ± 0.05 |
| 15 | 0.6 ± 0.02 | 0.2 ± 0.02 | 0.7 ± 0.05 | 0.5 ± 0.02 | 7.7 ± 0.15 |
| 20 | 0.7 ± 0.02 | 0.2 ± 0.05 | 1.8 ± 0.04 | 0.5 ± 0.01 | 11.0 ± 0.11 |
| 30 | 0.7 ± 0.02 | 0.4 ± 0.09 | 1.9 ± 0.05 | 2.3 ± 0.06 | 15.2 ± 0.23 |
| 45 | 0.8 ± 0.02 | 0.7 ± 0.24 | 7.0 ± 3.34 | 3.6 ± 0.10 | 20.8 ± 0 18 |
| 60 | 0.3 ± 0.06 | 1.0 ± 0.06 | 13.8 ± 0.04 | 12.7 ± 2.46 | 29.9 ± 0.30 |
| 75 | 1.2 ± 0.12 | 2.3 ± 0.64 | 14.0 ± 0.05 | 25.8 ± 1.99 | 41.9 ± 0.48 |
| 90 | 1.9 ± 0.6 | 3.8 ± 1.08 | 22.0 ± 1.33 | 36.4 ± 0.07 | 50.7 ± 0.47 |

TABLE 5

Mean ± SD (n = 4) Epi $AUC_{0-90\ min}$, J, P through porcine sublingual mucosa at various pH.

| Time (min) | pH 5 | pH 6 | pH 6.8 | pH 7.4 | pH 8 |
|---|---|---|---|---|---|
| $AUC_{0-90\ min}$ (μg/cm$^2$/ min) | 5169 ± 255* | 6191 ± 756* | 46562 ± 3450 | 60099 ± 6576 | 135689 ± 439 |

TABLE 5-continued

Mean ± SD (n = 4) Epi $AUC_{0-90\ min}$, J, P through porcine sublingual mucosa at various pH.

| Time (min) | pH 5 | pH 6 | pH 6.8 | pH 7.4 | pH 8 |
|---|---|---|---|---|---|
| J (µg/cm²/min) | 0.4 ± 0.1* | 0.8 ± 0.2* | 2.8 ± 0.2 | 5.3 ± 0.2 | 30.9 ± 0.4 |
| P (cm/min) | 0.02 ± 0.00* | 0.04 ± 0.01* | 0.14 ± 0.01 | 0.26 ± 0.01 | 1.54 ± 0.02 |

*$p < 0.05$ from pH 6.8, 7.4, and 8.

Example 3: Altering the Microenvironment pH of the Absorption Medium Using pH-Modifying Excipients Alkalizing (pH-modifying) excipients were selected and evaluated based on the desired pH values that resulted in optimal Epi stability and permeability from previous Examples 1 and 2.

Three pH modifiers were selected, sodium bicarbonate, calcium citrate, and sodium carbonate, and used in various percentages to determine in vitro the amount needed to modify the pH of a 2 mL water as a diffusion medium (n=3) with or without adding EpiBit equivalent to 20 mg Epi. The mean±SD of the medium pH was calculated.

The mean (±SD) of pH readings using various pH-modifying excipients with and without EpiBit equivalent to 20 mg Epi are presented in Table 6. Na Carbonate resulted in the highest mean (±SD) pH with the lowest needed percentage (0.75% w/v) with and without Epi, 8.6±0.2 and 11.7±0.0.

permeation of Epi through static vertical Franz diffusion cells at a controlled temperature of 37° C. as previously described in Example 2. EpiBit solution with or without a penetration enhancer was added to the donor chamber and phosphate buffer at pH 7.4 (pH of the blood) was used in the receiver chamber. Aliquots, 200 µL, were withdrawn from the receiver chamber at several time intervals. The volumes withdrawn were replenished with fresh phosphate buffer and the collected samples were filtered and transferred into HPLC vials for HPLC analysis using a UV detector. The cumulative amount of the Epi permeated over time ($AUC_{0-90min}$, µg/cm²/min), influx (J, µg/cm²/min), and permeability coefficient (P, cm/min) were calculated and statistically compared using ANOVA and Tukey-Kramer Tests.

Figure 6:
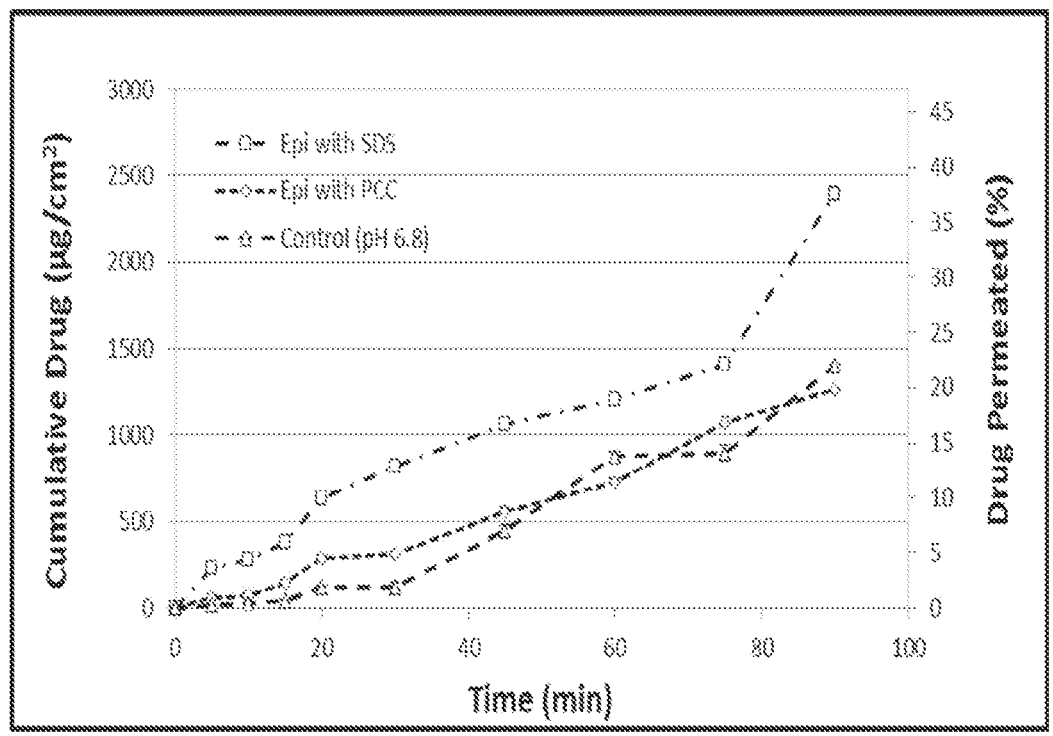
FIG. 6 is a graph illustrating cumulative permeated epinephrine and percentage through porcine sublingual mucosa over time with various permeation/penetration enhancers, Mean±SD (n=4).

The mean±SD (n=4) cumulative diffused Epi per area with different permeation enhancers are presented in Table 8 and FIG. 6. The Mean percentage of diffused Epi per area with different permeation enhancers were presented in Table 9 and FIG. 6.

TABLE 6

Mean ± SD (n = 3) of pH measurements using various pH-modifying excipients with and without epinephrine (20 mg).

| | pH Reading* | | | | | |
|---|---|---|---|---|---|---|
| | Na Bicarbonate | | Na Citrate | | Na Carbonate | |
| Concentration** | Without Epi | With Epi | Without Epi | With Epi | Without Epi | With Epi |
| 0.075% | 8.6 ± 0.06 | — | 7.4 ± 0.1 | — | — | — |
| 0.15% | 8.7 ± 0 06 | 4.5 ± 0.2 | 8.0 ± 0.3 | 3.7 ± 0.1 | 10 ± 0.0 | 4.7 ± 0.3 |
| 0.375% | 8.8 ± 0.06 | 4.9 ± 0.2 | 8.6 ± 0.1 | 4.1 ± 0.1 | 11.7 ± 0.1 | 6.8 ± 0.1 |
| 0.75% | 8.9 ± 0.0 | 6.9 ± 0.0 | 9.3 ± 0.1 | 4.8 ± 0.0 | 11.7 ± 0.0 | 8.6 ± 0.2 |
| 1.125% | 8.9 ± 0.1 | 7.9 ± 0.1 | 9.4 ± 0.1 | 5.0 ± 0.1 | | |
| 1.5% | 8.4 ± 0.1 | 7.3 ± 0.1 | 9.8 ± 0.0 | 6.6 ± 0.2 | | |
| 1.875% | 8.5 ± 0.1 | 7.7 ± 0.0 | 9.8 ± 0.1 | 7.1 ± 0.1 | | |
| 2.25% | 8.6 ± 0.1 | 7.9 ± 0.1 | — | — | | |

*Results presented as mean ± SD pH measurement in 2 mL water, equivalent to average saliva volume in 2 min.
**Percentage (w/v) was calculated for 2 mL water and EpiBit equivalent to 20 mg Epi.

Example 4: Effect of Penetration (Permeation) Enhancers on Epinephrine Sublingual Permeability The purpose was to evaluate the effect of different permeability enhancers on the sublingual permeability of Epi. Various penetration enhancers at different concentrations have been investigated to enhance drug permeation through buccal and sublingual routes (20). The effect of sodium dodecyl sulfate (SDS) and palmitoyl carnitine chloride (PCC), as penetration enhancers, on Epi sublingual permeability were evaluated. EpiBit (n=4) equivalent to 20 mg Epi and SDS (0.075% w/v) or PCC (1.2% w/v) were dissolved in 2 mL of phosphate buffer at pH 6.8 (average saliva pH). Epi permeability with no penetration enhancer was used as a control. Excised porcine sublingual membrane were used, as previously described in Example 2, to evaluate the

TABLE 8

Mean ± SD (n = 4) cumulative permeated epinephrine (20 mg) per area (µg/cm²) through porcine sublingual mucosa with various permeation enhancers.

| Time (min) | Control | Epi with SDS | Epi with PCC |
|---|---|---|---|
| 5 | 20.2 ± 1.2 | 228.0 ± 57.4 | 57.1 ± 9.3 |
| 10 | 27.9 ± 0.4 | 280.1 ± 122.3 | 71.9 ± 7.1 |
| 15 | 44.9 ± 3.0 | 380.8 ± 84.0 | 141.0 ± 12.9 |
| 20 | 115.3 ± 2.6 | 631.4 ± 116.0 | 285.7 ± 20.2 |
| 30 | 119.9 ± 2.9 | 817.7 ± 120.7 | 312.4 ± 17.2 |
| 45 | 447.5 ± 212.7 | 1059.2 ± 181.7 | 553.4 ± 27.2 |
| 60 | 877.6 ± 2.4 | 1202.1 ± 259. 7 | 726.7 ± 18.7 |
| 75 | 889.7 ± 3.2 | 1408.9 ± 339.9 | 1070.3 ± 31.7 |
| 90 | 1401.5 ± 85.0 | 2388.3 ± 327.3 | 1262.9 ± 17.7 |

TABLE 9

Mean ± SD (n = 4) percentage of diffused epinephrine (%) through porcine sublingual mucosa with various permeation enhancers.

| Time (min) | Control | Epi with SDS | Epi with PCC |
|---|---|---|---|
| 5 | 0.3 ± 0.02 | 3.6 ± 0.9 | 0.9 ± 0.1 |
| 10 | 0.4 ± 0.01 | 4.4 ± 1.9 | 1.1 ± 0.1 |
| 15 | 0.7 ± 0.05 | 6.0 ± 1.3 | 2.2 ± 0.2 |
| 20 | 1.8 ± 0.04 | 9.9 ± 1.8 | 4.5 ± 0.3 |
| 30 | 1.9 ± 0.05 | 12.8 ± 1.9 | 4.9 ± 0.3 |
| 45 | 7.0 ± 3.34 | 16.6 ± 2.9 | 8.7 ± 0.4 |
| 60 | 13.8 ± 0.04 | 18.9 ± 4.1 | 11.4 ± 0.3 |
| 75 | 14.0 ± 0.05 | 22.1 ± 5.3 | 16.8 ± 0.5 |
| 90 | 22.0 ± 1.33 | 37.5 ± 5.1 | 19.8 ± 0.3 |

Mean (±SD) $AUC_{0-90min}$, J, and P of permeated Epi with SDS 0.075% and PCC 0.75% were statistically higher ($p<0.05$) than the control. The $AUC_{0-90min}$, J, and P of permeated Epi with SDS enhancer were significantly higher ($p<0.05$) than with PCC enhancer (Table 10). Adding SDS 0.075% achieved the highest enhancement in Epi sublingual permeability and increased Epi permeability about 10-fold compared to control.

TABLE 10

Mean ± SD (n = 4) Epi $AUC_{0-90}$, J, P through porcine sublingual mucosa with various permeation enhancers.

| | Control | Epi with SDS | Epi With PCC |
|---|---|---|---|
| $AUC_{0-90\ min}$ (µg/cm²/min) | 46562 ± 3450* | 92365 ± 16594* | 52127 ± 670* |
| J (µg/cm²/min) | 2.8 ± 0.2* | 29 ± 4.3* | 8.7 ± 0.8* |
| P (/cm/min) | 0.14 ± 0.0* | 1.4 ± 0.2* | 0.4 ± 0.0* |

*p < 0.05 from all.

Penetration enhancers were able to enhance the sublingual permeability of Epi. SDS was superior to PCC in enhancing the sublingual permeability of Epi. The incorporation of a permeability enhancer into Epi formulation can significantly enhance the permeability and potentially the sublingual absorption of Epi as an alternative route of administration for the treatment of anaphylaxis and other conditions responsive to Epi.

Example 5: Combined Effect of a Penetration (Permeation) Enhancer and pH-Modification on Epinephrine Sublingual Permeability The combined effect of the alkalizing agent that was able to generate a pH value that resulted in optimal Epi sublingual permeability from previous Examples 2 and 3 with the penetration enhancer that resulted in optimal Epi sublingual permeability from previous Example 4 on the overall sublingual Epi permeability was evaluated. EpiBit equivalent to 20 mg Epi, 0.75% w/v sodium carbonate (Na Curb), as an alkalizing agent, and 0.075% w/v SDS, as a penetration enhancer, were dissolved in 2 ml, of deionized water based on results obtained from previous examples. Epi permeability from phosphate buffer at pH 6.8 with no penetration enhancer and no alkalizing agent from previous examples was used as a control. Excised porcine sublingual membranes were used, as described previously in Example 2, to evaluate the permeation of Epi through static vertical Franz diffusion cells at a controlled temperature of 37° C., as described previously in Example 2. EpiBit solution with penetration enhancer and alkalizing agent was added to the donor chamber. Phosphate buffer at pH 7.4 (pH of the blood) was used in the receiver chamber. Aliquots, 200 NL, were withdrawn from the receiver chamber at several time intervals. The volumes withdrawn were replenished with fresh phosphate buffer and the collected samples were littered and transferred into HPLC vials for HPLC analysis using a UV detector. The cumulative amount of the Epi permeated over time ($AUC_{0-90min}$, µg/cm²/min), influx (J, µg/cm²/min), and permeability coefficient (P, cm/min) were calculated and statistically compared with data of Epi permeability at pH 8 from Example 2, Epi permeability with 0.075% w/v SDS alone from Example 4, and control using ANOVA and Tukey-Kramer Tests.

Figure 7:
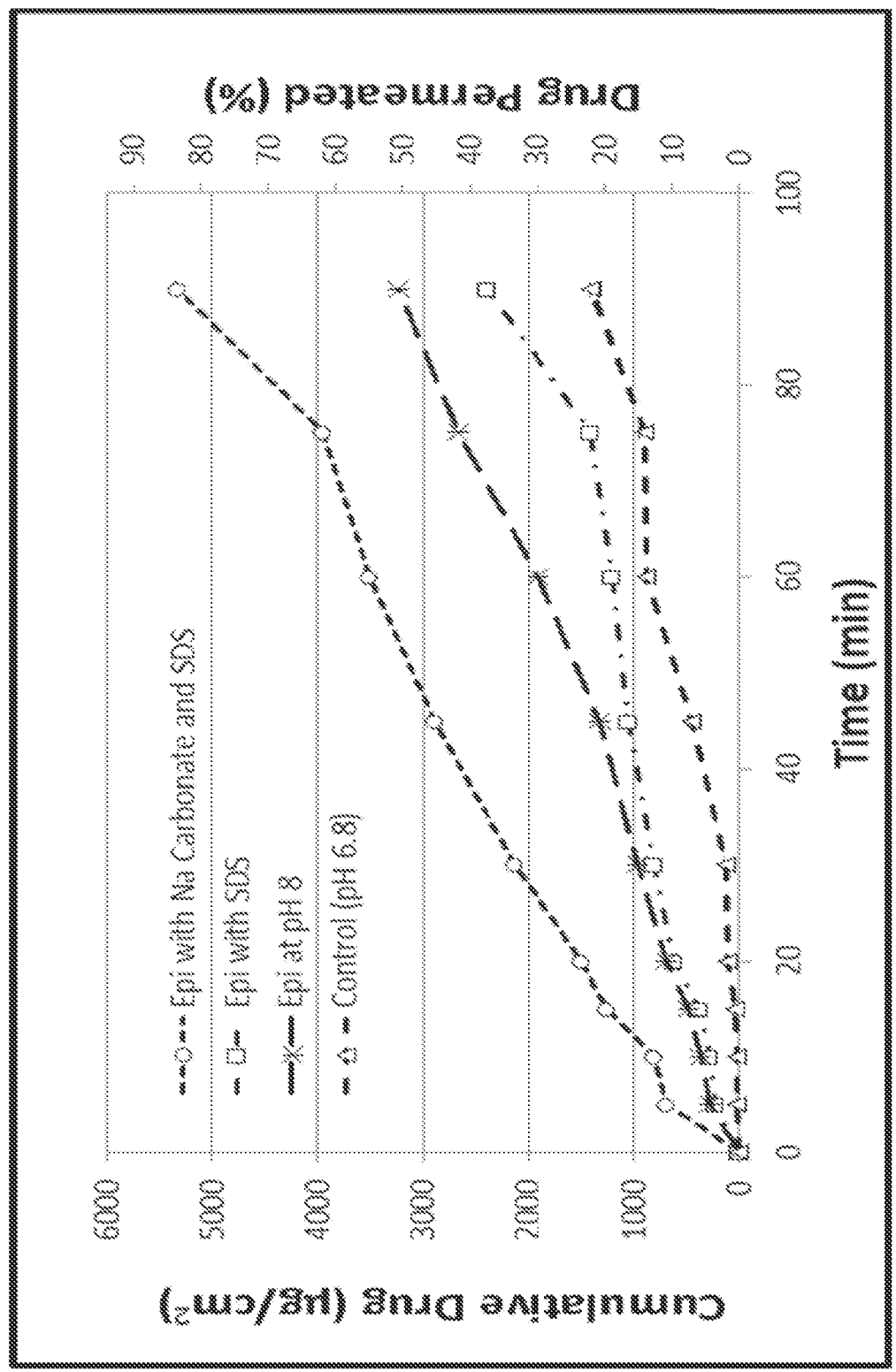
FIG. 7 is a graph illustrating cumulative permeated epinephrine and percentage through porcine sublingual mucosa over time with various formulations, Mean±SD (n=4).

The mean±SD (n=4) cumulative diffused Epi per area with alkalizing agent and permeation enhancer in comparison to Epi at pH 8, Epi with SDS only, and control are presented in Table 11 and FIG. 7. The Mean percentage of diffused Epi per area with alkalizing agent and permeation enhancer in comparison to Epi at pH 8, Epi with SDS only, and control were presented in Table 12 and FIG. 7.

TABLE 11

Mean ± SD (n = 4) cumulative permeated epinephrine (20 mg) per area (µg/cm²) through porcine sublingual mucosa from various formulations.

| Time (min) | Control | Epi at pH 8 | Ept with SDS | Epi with Na Carbonate and SDS |
|---|---|---|---|---|
| 5 | 20.2 ± 1.2 | 283.6 ± 1.7 | 228.0 ± 57.4 | 694.8 ± 72.5 |
| 10 | 27.9 ± 0.4 | 367.9 ± 3.0 | 280.1 ± 122.3 | 809.2 ± 51.1 |
| 15 | 44.9 ± 3.0 | 491.3 ± 9.3 | 380.8 ± 84.0 | 1263.2 ± 82.5 |
| 20 | 115.3 ± 2.6 | 700.0 ± 7.0 | 631.4 ± 116.0 | 1506.5 ± 32.4 |
| 30 | 119.9 ± 2.9 | 967.0 ± 14.4 | 817.7 ± 120.7 | 2139.8 ± 150.9 |
| 45 | 447.5 ± 212.7 | 1325.7 ± 11.7 | 1059.2 ± 181.7 | 2888.7 ± 448.4 |
| 60 | 877.6 ± 2.4 | 1902.2 ± 19.1 | 1202.1 ± 259.7 | 3515.9 ± 347.5 |
| 75 | 889.7 ± 3.2 | 2667.9 ± 30.7 | 1408.9 ± 339.9 | 3948.3 ± 139.2 |
| 90 | 1401.5 ± 85.0 | 3226.6 ± 29.9 | 2388.3 ± 327.3 | 5326.2 ± 47.4 |

TABLE 12

Mean ± SD (n = 4) percentage of diffused epinephrine (%) through porcine sublingual mucosa with various permeation enhancers.

| Time (min) | Control | Epi at pH 8 | Epi with SDS | Epi with Na Carbonate and SDS |
|---|---|---|---|---|
| 5 | 0.3 ± 0.02 | 4.5 ± 0.03 | 3.6 ± 0.9 | 10.9 ± 1.1 |
| 10 | 0.4 ± 0.01 | 5.8 ± 0.05 | 4.4 ± 1.9 | 12.7 ± 0.8 |
| 15 | 0.7 ± 0.05 | 7.7 ± 0.15 | 6.0 ± 1.3 | 19.8 ± 1.3 |
| 20 | 1.8 ± 0.04 | 11.0 ± 0.11 | 9.9 ± 1.8 | 23.7 ± 0.5 |
| 30 | 1.9 ± 0.05 | 15.2 ± 0.23 | 12.8 ± 1.9 | 33.6 ± 2.4 |

TABLE 12-continued

Mean ± SD (n = 4) percentage of diffused epinephrine (%) through porcine sublingual mucosa with various permeation enhancers.

| Time (min) | Control | Epi at pH 8 | Epi with SDS | Epi with Na Carbonate and SDS |
|---|---|---|---|---|
| 45 | 7.0 ± 3.34 | 20.8 ± 0.18 | 16.6 ± 2.9 | 45.4 ± 7.0 |
| 60 | 13.8 ± 0.04 | 29.9 ± 0.30 | 18.9 ± 4.1 | 55.2 ± 5.5 |
| 75 | 14.0 ± 0.05 | 41.9 ± 0.48 | 22.1 ± 5.3 | 62 0 ± 2.2 |
| 90 | 22.0 ± 1.33 | 50.7 ± 0.47 | 37.5 ± 5.1 | 83.6 ± 0.7 |

Mean (±SD) $AUC_{0-90min}$, J, and P of permeated Epi with Na Carbonate (0.75% w/v) and SDS (0.075% w/v) were statistically higher (p>0.05) than all. The J and P of permeated Epi with SDS enhancer alone and at pH 8 alone were significantly higher (p<0.05) than control but were not significantly different (p>0.05) from each other (Table 13). The combine effect of adding Na Carbonate (0.75% w/v) with SDS 0.075% on Epi sublingual permeability enhancement was significantly higher than using each one alone and increased Epi permeability about 25-fold compared to control.

TABLE 13

Mean ± SD (n = 4) Epi $AUC_{0-90\ min}$, J, P through porcine sublingual mucosa from various formulations.

|  | Control | Epi at pH 8 | Epi with SDS | Epi with Na Carbonate and SDS |
|---|---|---|---|---|
| $AUC_{0-90\ min}$ (µg/cm²/min) | 46562 ± 3450* | 135689 ± 439* | 92365 ± 16594* | 247123 ± 11900* |
| J (µg/cm²/min) | 2.8 ± 0.2* | 30.9 ± 0.4** | 29 ± 4.3** | 71.6 ± 0.6* |
| P (/cm/min) | 0.14 ± 0.0* | 1.54 ± 0.0** | 1.4 ± 0.2** | 3.6 ± 0.0* |

*p < 0.05 from all.
**p < 0.05 from control and Epi with Na Carbonate and SDS.

Example 6: Formulation of Epinephrine Sublingual Composition

A pediatric dose of epinephrine 15 mg and an adult dose of epinephrine 20 mg-40 mg, using epinephrine bitartrate salt, can be formulated as micronized or un-micronized particles with a particle size distribution ranging between 500 nm to 2.5 µm into a sublingual tablet formulation with or without a pH-modifier (alkalizer), with or without a penetration enhancer, with or without a flavor, and/or with or without a taste masking agent.

Example 6a: Formulation of Epinephrine Sublingual Table (15 mg) Including 27.29 mg of Epinephrine Bitartrate Salt, a pH Modifier, a Penetration Enhancer, a Flavor, and a Taste Masking Agent

| Ingredient | Type | Percentage (%) |
|---|---|---|
| active ingredient | Epinephrine Bitartrate | 24.26 |
| fillers | Ceolus, MCC (PH-F20JP) | 6.11 |
| fillers | Ceolus, MCC (UF-702) | 36.66 |
| flavor/sweetener | Mannitol | 14.5 |
| flavor | Grape | 0.5 |
| disintegrant | L-HPC (LH-NBD) (L-HPC:MCC, 1:9) | 5.89 |
| taste masking agent | Citric Acid (CA:API, 1:29) | 0.84 |
| penetration enhancer | SDS (1% of API) | 0.24 |
| akalizer | Na Carb | 10.0 |
| lubricant | Mg Stearate | 1.0 |
| Tablet Weight | | 100.0 |

Example 6b: Formulation of Epinephrine Sublingual Table (15 mg) Including 27.29 mg of Epinephrine Bitartrate Salt, a pH Modifier, a Penetration Enhancer, a Flavor, and a Taste Masking Agent

| Ingredient | Type | Percentage (%) |
|---|---|---|
| active ingredient | Epinephrine Bitartrate | 18.19 |
| fillers | Ceolus, MCC (PH-F20JP) | 6.93 |
| fillers | Ceolus, MCC (UF-702) | 41.55 |
| flavor/sweetener | Mannitol | 14.5 |
| flavor | Grape | 0.5 |
| disintegrant | L-HPC (LH-NBD) (L-HPC:MCC, 1:9) | 6.52 |
| taste masking agent | Citric Acid (CA:API, 1:29) | 0.63 |
| penetration enhancer | SDS (1% of API) | 0.18 |
| akalizer | Na Carb | 10.0 |
| lubricant | Mg Stearate | 1.0 |
| Tablet Weight | | 100.0 |

Example 6c: Formulation of Epinephrine Sublingual Table (15 mg) Including 27.29 mg of Epinephrine Bitartrate Salt, a pH Modifier, a Penetration Enhancer, a Flavor, and a Taste Masking Agent

| Ingredient | Type | Percentage (%) |
|---|---|---|
| active ingredient | Epinephrine Bitartrate | 24.26 |
| fillers | Ceolus, MCC (PH-F20JP) | 6.22 |

| Ingredient | Type | Percentage (%) |
|---|---|---|
| fillers | Ceolus, MCC (UF-702) | 37.31 |
| flavor/sweetener | Mannitol | 14.5 |
| flavor | Grape | 0.5 |
| disintegrant | L-HPC (LH-NBD) (L-HPC:MCC, 1:9) | 5.97 |
| taste masking agent | | |
| penetration enhancer | SDS (1% of API) | 0.24 |
| akalizer | Na Carb | 10.0 |
| lubricant | Mg Stearate | 1.0 |
| Tablet Weight | | 100.0 |

Example 6d: Formulation of Epinephrine Sublingual Table (15 mg) Including 27.29 mg of Epinephrine Bitartrate Salt, a pH Modifier, a Penetration Enhancer, a Flavor, and a Taste Masking Agent

| Ingredient | Type | Percentage (%) |
|---|---|---|
| active ingredient | Epinephrine Bitartrate | 18.19 |
| fillers | Ceolus, MCC (PH-F20JP) | 7.01 |
| fillers | Ceolus, MCC (UF-702) | 42.0 |
| flavor/sweetener | Mannitol | 14.5 |
| flavor | Grape | 0.5 |
| disintegrant | L-HPC (LH-NBD) (L-HPC:MCC, 1:9) | 6.58 |
| taste masking agent | | |
| penetration enhancer | SDS (1% of API) | 0.18 |
| akalizer | Na Carb | 10.0 |
| lubricant | Mg Stearate | 1.0 |
| Tablet Weight | | 100.0 |

Example 6e: Formulation of Epinephrine Sublingual Table (15 mg) Including 27.29 mg of Epinephrine Bitartrate Salt, a pH Modifier, a Penetration Enhancer, a Flavor, and a Taste Masking Agent

| Ingredient | Type | Percentage (%) |
|---|---|---|
| active ingredient | Epinephrine Bitartrate | 16.54 |
| fillers | Ceolus, MCC (PH-F20JP) | 7.15 |
| fillers | Ceolus, MCC (UF-702) | 42.89 |
| flavor/sweetener | Mannitol | 15.0 |
| flavor | | |
| disintegrant | L-HPC (LH-NBD) (L-HPC:MCC, 1:9) | 6.69 |
| taste masking agent | Citric Acid (CA:API, 1:29) | 0.57 |
| penetration enhancer | SDS (1% of API) | 0.2 |
| akalizer | Na Carb | 10.0 |
| lubricant | Mg Stearate | 1.0 |
| Tablet Weight | | 100.0 |

SUMMARY OF EXAMPLES

Epinephrine is suitable for sublingual administration and would have minimal or no significant degradation due to human saliva's pH and composition. Also, incorporating pH-modifying excipients into the tablet formulation would not compromise Epi stability (except between pH 4 to 5). They can be useful to adjust the variability in the pH of human saliva due to the consumption of various drinks with wide range of acidity and alkalinity. The incorporation of alkalizing agent to maintain the pH of the diffusion medium around 8 with a permeation enhancer like SDS into Epi sublingual table formulation can enhance the Epi sublingual permeability about 25-fold compared to about 10- to 11-fold increase for each one alone.

CONCLUSION

Epinephrine is an important medication in health systems worldwide for management of life-threatening allergies, i.e. anaphylaxis, cardiac events, i.e. cardiac arrest, and breathing difficulties, i.e. asthma, bronchial asthma, bronchitis, emphysema, and respiratory infections. The invention described and exemplified herein represents a new non-invasive sublingual drug delivery for epinephrine as a potential alternative, patient-friendly, convenient, and cost-effective dosage form, to the standard epi-autoinjectors.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, formulations, dosages, epinephrine fine particles, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

REFERENCES

1. Kemp S F, Lockey R F, Simons F E. Epinephrine: the drug of choice for anaphylaxis. A statement of the World Allergy Organization. Allergy. 2008; 63(8):1061-70.
2. McLean-Tooke A P, Bethune C A, Fay A C, Spickett G P. Adrenaline in the treatment of anaphylaxis: what is the evidence? BMJ. 2003;327(7427):1332-5.
3. Simons K J, Simons F E. Epinephrine and its use in anaphylaxis: current issues. Curr Opin Allergy Clin Immunol. 2010; 10(4):354-61.
4. Soar J, Pumphrey R, Cant A. Clarke S. Corbett A, Dawson P, et al. Emergency treatment of anaphylactic reactions—guidelines for healthcare providers. Resuscitation. 2008; 77(2):157-69.

5. Simons F E. Epinephrine auto-injectors: first-aid treatment still out of reach for many at risk of anaphylaxis in the community. Ann Alter Asthma Immunol. 2009; 102 (5):403-9.
6. Simons F E R. Lack of worldwide availability of epinephrine autoinjectors for outpatients at risk of anaphylaxis. Ann Allergy Asthma Immunol. 2005;94(5):534-8.
7. Korenblat P. Lundie M J, Dankner R E. Day J H. A retrospective study of epinephrine administration for anaphylaxis: how many doses are needed? Allergy Asthma Proc. 1999; 20(6):383-6.
8. Sicherer S H, Forman J A, Noone S A. Use assessment of self-administered epinephrine among food-allergic children and pediatricians. Pediatrics. 2000; 105(2):359-62.
9. Hoffman B B, Taylor P. Neurotransmission: The Autonomic and Somatic Motor Nervous Systems. In: Hardman J G, Limbird L E, Gilman A G, editors. Goodman & Gilman's The Pharmacological Basis of Therapeutics. 9 ed. New York: McGraw-Hill Companies, Inc.; 2001. p. 115-53.
10. Connors K A, Amidon G L, Stella V J. Chemical Stability of Pharmaceuticals: A Handbook for Pharmacists. 2 ed. New York: Wiley-Interscience Publication; 1986.438-47 p.
11. Bredenberg S, Duberg M, Lennernas B, Lennernas H, Pettersson A, Westerberg M, et al. In vitro and in vivo evaluation of a new sublingual tablet system for rapid oromucosal absorption using fentanyl citrate as the active substance. Eur J Pharm Sci. 2003; 20(3):327-34.
12. Glover E D, Glover P N, Franzon M, Sullivan C R, Cerullo C C, Howell R M, et al. A comparison of a nicotine sublingual tablet and placebo for smoking cessation. Nicotine Tob Res. 2002; 4(4):441-50.
13. Guez S. Efficacy of desensitization via the sublingual route in mite allergy. Chem Immunol Allergy. 2003; 82:62-76.
14. Saxena P, Salhan S. Sarda N. Sublingual versus vaginal route of misoprostol for cervical ripening prior to surgical termination of first trimester abortions. Eur J Obstet Gynecol Reprod Biol. 2006; 125(1):109-13.
15. Rawas-Qalaji M M, Simons F E, Simons K J. Fast-disintegrating sublingual epinephrine tablets: effect of tablet dimensions on tablet characteristics. Drug Dev Ind Pharm. 2007; 33(5):523-30.
16. Rawas-Qalaji M M, Simons F E R, Simons K J. Fast-Disintegrating Sublingual Tablets: Effect of Epinephrine Load on Tablet Characteristics. AAPS PharmSciTech. 2006; 7(2):E72-E8.
17. Birudaraj R, Berner B, Shen S, Li X. Buccal permeation of buspirone: mechanistic studies on transport pathways. J Pharr Sci. 2005; 94(1):70-8.
18. Diem K, Lentner C. Scientific Tables. 7ed. Basic, Switz.: Ciba-Geigy Limited; 1971.
19. Goswami T, Li X, Jasti B R. Effect of Lipophilicity and Drug Ionization on Permeation Across Porcine Sublingual Mucosa. AAPS PharmSciTech. 2017; 18(1):175-81.
20. Hassan N. Ahad A, Ali M, Ali J. Chemical permeation enhancers for transbuccal drug delivery. Expert Opin Drug Deliv. 2010; 7(1):97-112.
21. Epinephrine: Chemical and Physical Properties Bethesda, MD, USA PubChem. National Center for Biotechnology Information, U.S. National Library of Medicine; 2018 [https://pubchem.ncbi.nlnm.nih.gov/compound/5816#section=Chemical-and-Physical-Properties].
22. Rawwas-Qalaji M M. Simons F E, Simons K J. Sublingual epinephrine tablets versus intramuscular injection of epinephrine: Dose equivalence for potential treatment of anaphylaxis. J Allergy Clin Immunol. 2006; 117(2):398-403.
23. Atria M A, El-Gibaly I, Shaltout S E, Fetih G N. Transbuccal permeation, anti-inflammatory activity and clinical efficacy of piroxicam formulated in different gels. Int J Pharm. 2004; 276(1-2):11-28.
24. Nicolazzo J A, Reed B L, Finnin B C. Assessment of the effects of sodium dodecyl sulfate on the buccal permeability of caffeine and estradiol. J Pharm Sci. 2014; 93(2):431-40.
25. Duizer E, van der Wulp C, Versantvoort C H, Groten J P. Absorption enhancement, structural changes in tight junctions and cytotoxicity caused by palmitoyl carnitine in Caco-2 and IEC-18 cells. J Pharmacol Exp Ther. 1998; 287(1):395-402.
26. Sutton S C, LeCluyse E L, Cammack L, Fix J A. Enhanced bioavailability of cefoxitin using palmitoyl L-carnitine. I. Enhancer activity in different intestinal regions. Pharm Res. 1992; 9(2):191-4.
27. Swenson E S, Milisen W B, Curatolo W. Intestinal permeability enhancement: efficacy, acute local toxicity, and reversibility. Pharm Res. 1993; 11(8):1132-42.
28. R. H. Müller et al. Eur J Pharm Biopharm 78(1):1-9 2011.

What is claimed is:

1. A sublingual composition formulated as a fast-disintegrating tablet, the sublingual composition comprising:
    epinephrine bitartrate fine particles having a particle size distribution in a range from about 500 nm to about 2.5 um;
    an alkalizing excipient for increasing pH at a site of administration of the sublingual composition, wherein the alkalizing excipient consists of sodium carbonate added to the sublingual composition at 0.75% w/v; and
    a penetration enhancer, wherein the penetration enhancer is sodium dodecyl sulfate (SDS) added to the sublingual composition at 0.075% w/v or palmitoyl carnitine chloride (PCC) added to the sublingual composition at 1.2% w/v.

2. The sublingual composition according to claim 1, wherein the epinephrine bitartrate fine particles have a dosage equivalent to a range of about 15 mg epinephrine to about 20 mg epinephrine.

3. The sublingual composition according to claim 1, further comprising at least one of a filler, a flavor, a sweetener, a disintegrant, a taste masking agent, and a lubricant.

4. A method for treating a condition responsive to epinephrine in a subject in need thereof, the method comprising:
    providing the sublingual composition according to claim 1; and
    administering the sublingual composition to the subject, thereby treating the condition responsive to epinephrine in the subject.

5. The method according to claim 4, wherein the condition responsive to epinephrine is anaphylaxis, a cardiac event, an allergy, or a breathing difficulty.

* * * * *